United States Patent [19]

Wadsworth et al.

[11] Patent Number: 5,091,397
[45] Date of Patent: Feb. 25, 1992

[54] NOVEL COMPOUNDS

[75] Inventors: Harry J. Wadsworth; Michael S. Hadley; Paul A. Wyman; Sarah M. Jenkins, all of Harlow, England

[73] Assignee: Beecham Group p.l.c., Brentford, England

[21] Appl. No.: 415,123

[22] Filed: Sep. 29, 1989

[30] Foreign Application Priority Data

Oct. 3, 1988 [GB] United Kingdom ............... 8823142
Sep. 7, 1989 [GB] United Kingdom ............... 8920073

[51] Int. Cl.$^5$ .................. C07D 487/08; A61K 31/41; A61K 31/42; A61K 31/425
[52] U.S. Cl. ..................... 514/359; 514/361; 514/363; 514/364; 514/365; 514/372; 514/374; 514/378; 514/381; 514/413; 548/128; 548/131; 548/136; 548/143; 548/181; 548/214; 548/235; 548/247; 548/254; 548/255; 548/453
[58] Field of Search ............... 548/131, 143, 235, 247, 548/120, 136, 181, 214, 254, 255, 453; 514/306, 374, 378, 361, 363, 365, 372, 381, 359, 413

[56] References Cited

FOREIGN PATENT DOCUMENTS 261763  3/1988  European Pat. Off. ............ 548/133
301729  2/1989  European Pat. Off. ............ 548/133

*Primary Examiner*—Robert Gerstl
*Attorney, Agent, or Firm*—Hopgood, Calimafde, Kalil, Blaustein & Judlowe

[57] ABSTRACT

A compound of formula (I) or a pharmaceutically acceptable salt thereof:

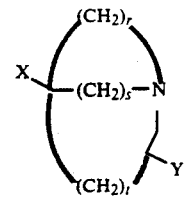

in which one of X and Y represents hydrogen and the other represents —$CH_2$—Z where Z is a group

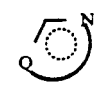

in which Q represents a 3-membered divalent residue completing a 5-membered aromatic ring and comprises one or two heteroatoms selected from oxygen, nitrogen and sulphur, or three nitrogen atoms, any amino nitrogen being optionally substituted by a $C_{1-2}$ alkyl, cyclopropyl or propargyl group, and any ring carbon atom being optionally substituted by a group $R_1$; or a group

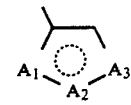

in which $A_1$, $A_2$ and $A_3$ complete a 5-membered aromtic ring and $A_1$ is oxygen or sulphur, one of $A_2$ and $A_3$ is $CR_2$ and the other is nitrogen or $CR_3$, or $A_2$ is oxygen or sulphur, one of $A_1$ and $A_3$ is $CR_2$ and the other is $CR_3$; and $R_1$, $R_2$ and $R_3$ are independently selected from hydrogen, halogen, CN, $OR_4$, $SR_4$, $N(R_4)_2$, $NHCOR_4$, $NHCOOCH_3$, $NHCOOC_2H_5$, $NHOR_4$, $NHNH_2$, $NO_2$, $COR_4$, $COR_5$, $C_{2-4}$ alkenyl, $C_{2-4}$ alkynyl, cyclopropyl or $C_{1-2}$ alkyl optionally substituted with $OR_4$, $N(R_4)_2$, $SR_4$, $CO_2R_4$, $CON(R_4)_2$ or one, two or three halogen atoms, in which each $R_4$ is independently hydrogen or $C_{1-2}$ alkyl and $R_5$ is $OR_4$, $NH_2$ or $NHR_4$; r represents an integer of 2 or 3, s represents an integer of 1 or 2 and t represents 0 or 1, with the proviso that when Y is hydrogen s is 1.

9 Claims, No Drawings

NOVEL COMPOUNDS

This invention relates to compounds having pharmaceutical activity, to a process for their preparation and their use as pharmaceuticals.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

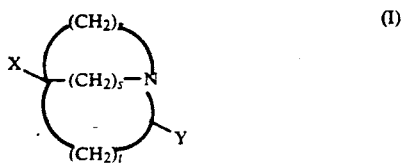

in which one of X and Y represents hydrogen and the other represents —CH$_2$—Z where Z is a group

in which Q represents a 3-membered divalent residue completing a 5-membered aromatic ring and comprises one or two heteroatoms selected from oxygen, nitrogen and sulphur, or three nitrogen atoms, any amino nitrogen being optionally substituted by a C$_{1-2}$ alkyl, cyclopropyl or propargyl group, and any ring carbon atom being optionally substituted by a group R$_1$; or a group

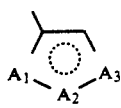

in which A$_1$, A$_2$ and A$_3$ complete a 5-membered aromatic ring and A$_1$ is oxygen or sulphur, one of A$_2$ and A$_3$ is CR$_2$ and the other is nitrogen or CR$_3$, or A$_2$ is oxygen or sulphur, one of A$_1$ and A$_3$ is CR$_2$ and the other is CR$_3$; and R$_1$, R$_2$ and R$_3$ are independently selected from hydrogen, halogen, CN, OR$_4$, SR$_4$, N(R$_4$)$_2$, NHCOR$_4$, NHCOOCH$_3$, NHCOOC$_2$H$_5$, NHOR$_4$, NHNH$_2$, NO$_2$, COR$_4$, COR$_5$, C$_{2-4}$ alkenyl, C$_{2-4}$ alkynyl, cyclopropyl or C$_{1-2}$ alkyl optionally substituted with OR$_4$, N(R$_4$)$_2$, SR$_4$, CO$_2$R$_4$, CON(R$_4$)$_2$ or one, two or three halogen atoms, in which each R$_4$ is independently hydrogen or C$_{1-2}$ alkyl and R$_5$ is OR$_4$, NH$_2$ or NHR$_4$; r represents an integer of 2 or 3, s represents an integer of 1 or 2 and t represents 0 or 1, with the proviso that when Y is hydrogen s is 1. The term halogen includes bromine, chlorine and fluorine.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

In compounds of formula (I) having two asymmetric centres where Y is other than hydrogen, the stereochemical configuration in which the group Y and the (CH$_2$)s bridge are on the same side of the plane of the molecule which contains both bridgehead atoms and the ring carbon atom bonded to the group Y will herein be referred to as the exo configuration. Similarly, the configuration of compounds in which the group Y and the bridge (CH$_2$)s are on opposite sides of the above-mentioned plane of the molecule will herein be referred to as the endo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (r, s, t) include (2,2,0), (3,1,0), (2,1,0), (2,1,1) and (3,1,1), most preferably (2,1,0).

Examples of combinations of (r, s, t) include (2,1,0), (3,1,0), (2,1,1) and (2,2,0).

X is preferably hydrogen.

5-Membered aromatic heterocycles within the definition of variable Z include oxadiazole such as 1,2,4-oxadiazol-5-yl, 1,2,4-oxadiazol-3-yl and 1,3,4-oxadiazol-2-yl, oxazole such as 1,3-oxazol-2-yl, 1,3-oxazol-4-yl 1,3-oxazol-5-yl, 1,2-oxazol-3-yl and 1,2-oxazol-5-yl, thiadiazole such as 1,2,4-thiadiazol-5-yl and 1,3,4-thiadiazol-2-yl, thiazole such as 1,3-thiazol-2-yl, 1,3-thiazol-5-yl and 1,2-thiazol-5-yl and furan such as furan-2-yl and furan-3-yl, triazole such as 1,2,3-triazol-4-yl and 2H-tetrazol-5-yl.

In a preferred aspect, variables R$_1$, R$_2$ and R$_3$ are independently selected from hydrogen, halogen, N(R$_4^1$)$_2$, C$_{2-3}$ alkenyl, C$_{2-3}$ alkynyl, cyclopropyl or C$_{1-2}$ alkyl optionally substituted with one, two or three fluorine atoms, in which R$_4^1$ is hydrogen or methyl.

Values for R$_1$, R$_2$ and R$_3$ include hydrogen, methyl, ethyl, NH$_2$ and CH$_2$F, preferably hydrogen, methyl and NH$_2$, most preferably hydrogen and methyl.

It will be appreciated that the range of values for R$_1$, R$_2$ and R$_3$ will be limited by the preparative constraints and/or stability of the group Z. For example, a 1,3-oxazole ring will tolerate a 2-amino substituent whereas 2-amino furans are unstable. Conversely, 2-halo-furans are stable whereas 2-halo-1,3-oxazoles are very labile compounds. Where Z is a tri- or tetrazole group, the amino nitrogen must be substituted, preferably γ to the position of the methyl-azabicyclic moiety.

Examples of Z include 3-amino-1,2,4-oxadiazol-5-yl, 3-methyl-1,2,4-oxadiazol-5-yl, 1,3-oxazol-2-yl, 1,3-oxazol-5-yl, 2-methyl-2H-tetrazol-5-yl, 2-furyl, 5-methyl-1,2,4-oxadiazol-3-yl and 1,3-thiazol-2-yl.

The invention also provides a process for the preparation of a compound of formula (I), or a pharmaceutically acceptable salt thereof, which process comprises:

(a) cyclising a compound of formula (II):

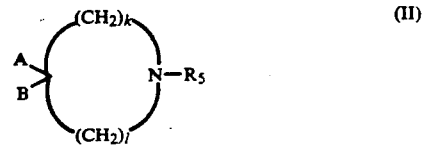

in which (i) A represents CH$_2$Z or a group convertible thereto and B represents —(CH$_2$)$_j$L$_1$ where L$_1$ is a leaving group or A and L$_1$ together represent —COO—;

one of j, k and l is 1 and the other two independently represent an integer of 2 or 3, and $R_5$ represents hydrogen or an N-protecting group; to give a compound of formula (IIa):

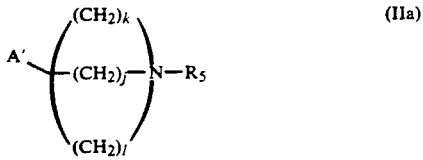

in Which A' represents $CH_2Z$ or a group convertible thereto, $x^-$ is an anion and the remaining variables are as previously defined;

or (ii) A represents an electron withdrawing group, B represents hydrogen and $R_5$ represents $-(CH_2)_j L_2$ where $L_2$ is a leaving group; one of k and l is 1 and the other and j independently represent an integer of 2 or 3; to give a compound of formula (IIb):

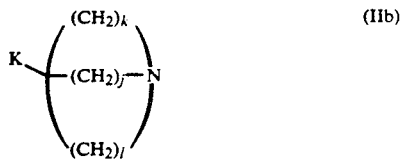

in which K represents an electron withdrawing group or A' and the remaining variables are as previously defined;

and thereafter, optionally or as necessary, removing any $R_5$ N-protecting group, converting K to A', converting A' to $CH_2Z$, interconverting Z and/or forming a pharmaceutically acceptable salt;

(b) cyclising a compound of formula (III):

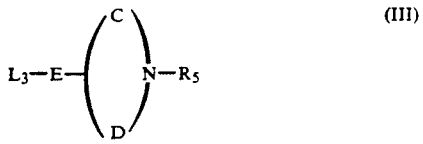

where $R_5$ is hydrogen or an N-protecting group, and either C is one, D is another and E is the remainder of $-(CH_2)_r-$, $-(CH_2)_s-$ and $-(CH_2)_t-CH(CH_2Z)-CH_2-$ or groups convertible thereto, and $L_3$ is a leaving group; or C is one and E is the other of $-(CH_2)_r-$ and $-(CH_2)_s-$ or groups convertible thereto and D represents $-(CH_2)_t-CHA-CH_2-$ where A' and $L_3$ together represent $-COO-$, and thereafter, optionally or as necessary and in any appropriate order, converting C, D and E to $-(CH_2)_r-$, $-(CH_2)_s-$ and $-(CH_2)_t-CH(CH_2Z)-CH_2-$, removing any $R_5$ protecting group, interconverting Z and/or forming a pharmaceutically acceptable salt; or (c) cyclising a compound of formula (IV):

where F is one and G is the other of $-(CH_2)_r-$ and $-(CH_2)_s-$ or groups convertible thereto, and one of $Y_3$ and $Y_4$ is $-(CH_2)_u-K$ and the other is $-(CH_2)_v-$ $(CO)_yL_4$ where K is an electron withdrawing group, $L_4$ is a leaving group, and u, v and y are independently 0 or 1, with the proviso that when $Y_4$ is $(CH_2)_u-K$, u is 1 and when $Y_4$ is $-(CH_2)_v(CO)_yL_4$, v and y are 1, and thereafter, optionally or as necessary and in any appropriate order, where y is 1, hydrolysing and decarboxylating the cyclisation product and converting the $C=O$ group to $CH-CH_2Z$, where y is 0, converting K to $CH_2Z$, converting F and G to $-(CH_2)_r-$ and $-(CH_2)_s-$ as appropriate, interconverting Z and/or forming a pharmaceutically acceptable salt, u, v and y being such that the desired compound of formula (I) is obtained.

The deprotection, conversion and interconversion steps may be carried out in any appropriate order.

In process Variant (a), examples of the leaving groups $L_1$ and $L_2$ include halo such as bromo, tosyloxy and mesyloxy.

Examples of $R_5$ when an N-protecting group include benzyl and substituted benzyl.

Examples of A and A' include alkoxycarbonyl, benzyloxycarbonyl and cyano.

The cyclisation reaction is a nucleophilic substitution which may be carried out under conventional conditions appropriate to the groups A and B. Thus, when B is $(CH_2)_jBr$ and A is $C_{1-4}$ alkoxycarbonyl, the cyclisation is carried out in an inert solvent such as toluene or ether at elevated temperature. When B is $(CH_2)_jOTos$ or $(CH_2)_jO$-Mes, it is preferably obtained by treatment of a $(CH_2)_jOH$ group with a suitable reagent such as tosylchloride or mesyl chloride, in a base such as pyridine, whereupon the cyclisation may proceed at ambient temperature, or at elevated temperature in an inert solvent such as toluene. When A and $L_1$ together represent $-COO-$, the cyclisation may be carried out in a lower alkanol such as ethanol in the presence of acid such as hydrogen bromide. In the resulting compound of formula (IIa), A' will be an alkoxycarbonyl group corresponding to the lower alkanol used for the cyclisation.

Where $R_5$ is an N-protecting group such as benzyl, this may be removed by conventional hydrogenation, preferably catalytically over a suitable catalyst such as Pd/C. Where A' or K is benzyloxycarbonyl, deesterification and deprotection may be effected simultaneously by conventional hydrogenation.

Examples of K and A when an electron withdrawing group include $C_{1-4}$ alkoxycarbonyl and cyano.

When A is an electron withdrawing group such as $C_{1-4}$ alkoxycarbonyl, B is hydrogen and $R_5$ is $-(CH_2)_jL_2$ where $L_2$ is, for example, chloro, the cyclisation may be effected by treatment of the compound of formula (II) with lithium diisopropylamide.

In process variant (b), examples of leaving groups $L_3$ include halo such as chloro and hydroxy. Examples of groups convertible to $-(CH_2)_t-CH(CH_2Z)CH_2-$ include $-(CH_2)_tCOCH_2-$ and $-(CH_2)_tCHA'CH_2-$. In the group $-(CH_2)_t-CHA'-CH_2-$, examples of A' include hydroxy, $C_{1-4}$ alkoxycarbonyl, cyano and formyl. In process variant (c), examples of $L_4$ include those given for $L_3$ or $C_{1-4}$ alkoxy such as ethoxy. Examples of electron withdrawing groups K include $C_{1-4}$ alkoxycarbonyl and cyano.

In process variant (b), where $L_3$ is hydroxy and D is $-(CH_2)_t-CHOH-CH_2-$, the cyclisation of compounds of formula (III) may be carried out by pyrolysis, by the method of D.O. Spry and H.S. Aaron, J. Org.

Chem., 1969, 34, 3674, to yield a compound where A' is hydroxy.

Where E is —(CH$_2$)$_r$—CO—CH$_2$—, the cyclisation may be carried out under basic conditions where R$_5$ is benzyl (F.I. Carrol, A.M. Ferguson, and J.B. Lewis, J. Org. Chem. 31. 2957, 1966).

Where L$_3$ and A' together represent —COO—, the cyclisation is a rearrangement reaction which can be carried out under acid conditions in a polar solvent, such as hydrogen bromide in ethanol, at ambient temperature, to yield a compound where A' is a carboxy ester group. It is preferred to protect the nitrogen atom with an R$_5$ N-protecting group such as benzyl, which may be subsequently removed by hydrogenation over a suitable catalyst such as Pd/C.

In process variant (c), where Y$_3$ and Y$_4$ both contain carboxy ester groups the cyclisation of compounds of formula (IV) is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

Where y is 0, the cyclisation may be carried out as described in EP-0094742 under basic conditions such as sodium hydride and potassium t-butoxide, in an inert polar solvent such as dimethylformamide.

Conversions of groups A' and K and of the carbonyl group from process variants (b) and (c), and interconversions of Z, may be carried out conventionally, see for example standard text books on heterocyclic chemistry such as 'Comprehensive Heterocyclic Chemistry', A.R. Katritzky and C.W. Rees, Pergamon, 1984.

The groups A' and K are first converted to a group CH$_2$Z' where Z' is Z or a group convertible thereto. The carbonyl group from process variants (b) and (c) is converted to a group C=CH—Z' or CH—CH$_2$—Z' where Z' is as aforesaid.

A carbonyl group may be reacted with tosylmethyl isocyanide to yield a compound where A' is cyano, or with methoxymethyl triphenyl phosphonium chloride and potassium t-butoxide in dimethyl formamide followed by aqueous acid hydrolysis of the enol ether to yield a compound where A' is formyl.

Alternatively the carbonyl group may be reduced to an A' hydroxy group with a suitable reducing agent such as sodium borohydride in ethanol at ambient temperature, or sodium in ethanol at elevated temperature, such as the boiling point of the solvent, under an inert atmosphere such as nitrogen, depending on the stereochemistry required.

An A' hydroxy group may be converted to cyano by first converting it to a good leaving group such as mesyloxy or tosyloxy and then displacing it with cyanide ion.

An A' formyl group may be obtained by conventional reduction of an A' or K alkoxycarbonyl group with a reducing agent such as diisobutylaluminium hydride in an inert solvent such as toluene at low temperature, or, more preferably hydrolysis with acid, followed by conversion to the acid chloride by treatment with thionyl chloride and reaction with O-N-methylated dimethyl hydroxylamine hydrochloride in the presence of pyridine in a suitable solvent such as dichloromethane to give the O-N-dimethyl amide. Reduction with diisobutyl aluminium hydride under similar conditions as above yields the required formyl group.

An A' formyl group may be converted to CH$_2$CN by treatment with p-toluenesulphonylmethyl isocyanide under basic conditions at depressed temperature.

A Z 2-furyl or 1,3-thiazol-2-yl group may be obtained by treatment of an A' formyl group with the anion of the heterocycle. In the case of 2-furyl, the lithium salt of furan is generated by treatment of furan with lithium diisopropylamide or butyl lithium, followed by treatment of the resulting secondary alcohol with a Lewis acid such as tin (IV) chloride to afford the carbonium ion which is reduced with a hydride donor such as triethyl silane. In the case of 1,3-thiazol-2-yl, 2-trimethylsilyl-1,3-thiazole is used and the secondary alcohol is dehydrated and the resulting olefin is catalytically hydrogenated.

In one preferred aspect, the process comprises:
(d) the reaction of a compound of formula (V):

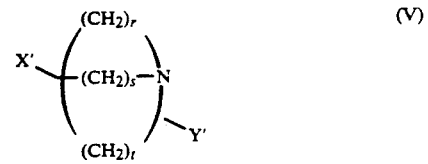

in which r, s and t are as defined in formula (I); one of X' and Y' represents hydrogen and the other represents a halocarbonyl group, with diazomethane, followed by catalytic rearrangement of the resulting diazoketone in the presence of water, an alcohol or an amine; or
(e) the reaction of

in which J represents —(CH$_2$)$_r$—CO—CH$_2$— and r, s and t are as defined for formula (I), with a phosphorus ylide of formula (VII) or (VII):

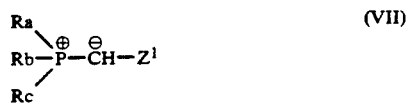

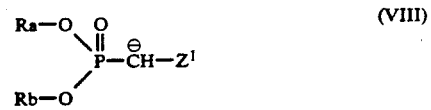

in which Ra, Rb and Rc are independently C$_{1-6}$ alkyl, aryl or aralkyl and Z$^1$ is a carboxylic acid, or ester or amide derivative thereof, followed by optional interconversion of Z$^1$, reduction of the resulting α,β-unsaturated acid, or ester or amide derivative thereof; the product of process variant (d) being a compound of formula (IX):

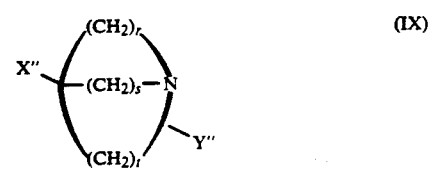

in which r, s and t are as defined for formula (I), one of X" and Y" represents hydrogen and the other represents —$CH_2$—$Z^1$ where $Z^1$ is as defined for formulae (VII) and (VIII), and the product of process variant (e) being a compound of formula (IX) in which r, s and t are as defined for formula (I), X" is hydrogen and Y" represents —$CH_2$—$Z^1$ where $Z^1$ is as defined for formulae (VII) and (VIII); and thereafter converting $Z^1$ to Z, optionally interconverting Z and/or forming a pharmaceutically acceptable salt.

The halocarbonyl group in the compound of formula (V) may be obtained by conversion of an A' alkoxycarbonyl group by conventional de-esterification followed by halogenation with a suitable reagent such as thionyl chloride, or by conversion of an A' cyano group by conventional acid hydrolysis to the carboxylic acid followed by halogenation as aforesaid.

Conversion of a compound of formula (V) to a compound of formula (IX) which is equivalent to the conversion of an acyl halide to a carboxylic acid or derivative thereof having one additional carbon atom is known as the Arndt-Eistert Synthesis and may be carried out under conditions commonly used for that synthesis. The synthesis proceeds via a diazoketone intermediate which rearranges in the presence of a catalyst, for example silver oxide to a ketene which reacts with water to form a carboxylic acid, or alternatively with an alcohol, for example ethyl alcohol, to form an ester derivative or with an amine, for example ammonia, to form an amide derivative.

The reaction of a compound of formula (VI) with a phosphorus ylide of formula (VII) or (VIII) which is equivalent to the conversion of a ketone to an olefin is known as a Wittig Reaction and may be carried out under conditions generally used for such reactions. Preferably a compound of formula (VI) is reacted with a compound of formula (VIII) in which Ra and Rb are each $C_{1-6}$ alkyl, for example ethyl, and $Z^1$ is an ester function, for example ethoxycarbonyl. The resulting olefin may be reduced under standard conditions, for example by catalytic hydrogenation in an alcoholic solvent such as ethanol in the presence of a noble metal catalyst such as palladium or by treatment with magnesium and methanol, according to the stereochemistry required.

Where it is required that $Z^1$ in the compound of formula (IX) is an amide derivative, it may be convenient to use a compound of formula (VII) or (VIII) in which $Z^1$ is an amide derivative or alternatively to convert a $Z^1$ ester to a $Z^1$ amide by treatment with ammonia prior to reduction of the $\alpha,\beta$-unsaturated intermediate.

While it is preferred to reduce the $\alpha,\beta$-unsaturated acid, or ester or amide derivative thereof, it will be appreciated that conversion of $Z^1$ to Z may take place prior to the reduction of the double bond.

Conversion of Z' to a heterocyclic group Z, as defined for formula (I), may be carried out using procedures as described in, for example standard text books on heterocyclic chemistry such as 'Comprehensive Heterocyclic Chemistry', A.R. Katritzky and C.W. Rees, Pergamon, 1984.

The Z' group is first converted, as necessary, to a suitable starting group Z' for the chosen conversion reaction to give the required group Z.

A Z' alkoxycarbonyl group may be obtained by conventional acid hydrolysis of a Z' cyano group followed by esterification.

A Z' carboxy group may be obtained by conventional de-esterification of a Z' alkoxycarbonyl group.

A Z' chlorocarbonyl group may be obtained by treatment of a Z' carboxy group with thionyl chloride at elevated temperature.

A Z' aminocarbonyl group may be obtained by treatment of a Z' chlorocarbonyl group with ammonia.

A Z' cyano group may be obtained by treatment of a Z' aminocarbonyl group with a dehydrating agent such as phosphorus pentoxide in toluene, or pyridine and trifluoroacetic anhydride.

A Z' $CH_3CO$— group may be obtained by treatment of a LiOOC group with methyl lithium, the LiOOC group being obtained by hydrolysis of a Z' alkoxycarbonyl group with lithium hydroxide in water. Alternatively, a Z' $CH_3CO$— group may be obtained by reaction of a Z' chlorocarbonyl group with N,O-dimethylhydroxylamine and treatment with methyl lithium.

A Z' bromomethylcarbonyl group may be obtained by treatment of a Z' $COCH_3$ group either with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively, a Z' —COCl group may be converted to a —$COCH_2Br$ group by treatment with diazomethane in ether at low temperature followed by hydrogen bromide in acetic acid at ambient temperature.

A Z' $CH_2N\equiv C$ group may be obtained from a formamidomethyl group by treatment with phosgene and triethylamine. The formamidomethyl group may in turn be obtained from the aminomethyl group by reaction with an ester of formic acid such as ethyl formate. The aminomethyl group may be obtained by reduction of the aminocarbonyl group with lithium aluminium hydride.

A Z' formyl group may be obtained from a Z' alkoxycarbonyl group as described above for the corresponding conversion of an A' alkoxycarbonyl group.

When Z represents a 1,2,3-triazol-4-yl group, a Z' formyl group may be treated with triphenyl phosphine, carbon tetrabromide and zinc in an inert solvent such as dichloromethane at ambient temperature to provide a 2,2-dibromoethenyl group which may be eliminated with n-butyl lithium in hexane to give an ethynyl group. Treatment of the latter with azidotrimethyl silane in an inert solvent such as tetrahydrofuran at elevated temperature yields the unsubstituted 1,2,3-triazol-4-yl group which is alkylated as required. A 2-methyl group may be introduced by treatment with diazomethane in ether at ambient temperature.

When Z represents a 2H-tetrazol-5-yl group, a Z' cyano group may be treated with azidotrimethyl silane in an inert solvent such as tetrahydrofuran at elevated temperature to yield a 2-trimethylsilyl-2H-tetrazol-5-yl group. Treatment of the latter with methanol effects deprotection of the amino nitrogen which may then be alkylated as described above.

When Z represents 3-substituted-1,2,4-oxadiazol-5-yl, a Z' chlorocarbonyl or Z' carboxy ester group may be reacted with an appropriate amide oxime, at elevated temperature in an inert, polar solvent such as chloroform, and the resulting substitution product cyclised at elevated temperature in a suitable solvent such as toluene or xylene.

For example, when Z represents 3-methyl-1,2,4-oxadiazol-5-yl, a Z' chlorocarbonyl group may be reacted with acetamide oxime, at elevated temperature in an inert, polar solvent such as chloroform, and the resulting substitution product cyclised at elevated temperature in a suitable solvent such as toluene or xylene. Alternatively, reaction of a Z' aminocarbonyl group with an acetal of N,N-dimethylacetamide such as the dimethyl or diethyl acetal at elevated temperature yields an acyl amidine group $-CON=C(CH_3)N(CH_3)_2$ which may then be cyclised with hydroxylamine, in the presence of acid, such as acetic acid, which may also function as the solvent. The reaction may be carried out at ambient temperature, the N-hydroxy acyl amidine intermediate isolated and then cyclised at elevated temperature, or alternatively in a single step at elevated temperature. When Z represents 3-amino-1,2,4-oxadiazol-5-yl, a Z' chlorocarbonyl or Z' carboxy ester group may be reacted with a hydroxy guanidine derivative under basic conditions.

When Z represents 3-(H or methyl)-1,2,4-thiadiazol-5-yl, a Z' aminocarbonyl group may be converted into an aminothiocarbonyl group using phosphorus pentasulphide or Lawesson's reagent (S. Scheibye, B.S. Pederson and J.O. Lawesson, Bull. Soc. Chim. Belg., 1978, 87 (3), 229). The aminothiocarbonyl may be converted into a thioacyl amidine group and cyclised as described above for the 1,2,4-oxadiazole group.

When Z represents 5-($C_{1-2}$alkyl)-1,2,4-oxadiazol-3-yl, a Z' cyano group may be reacted with hydroxylamine, in a polar solvent such as methanol, to yield the corresponding amide oxime. The amide oxime may be cyclised using a suitable derivative of a $C_{2-3}$ alkanoic such as the anhydride or a trialkylorthoacetate such as triethyl orthoacetate, the acid derivative acting as the solvent, at elevated temperature.

When Z represents 5-(H or $C_{1-2}$alkyl)-1,3,4-oxadiazol-2-yl, a Z' carboxy or carboxy ester group may be converted to the acid hydrazide by conventional procedures. For example, the acid may be converted to a $C_{1-6}$ alkyl ester e.g. methyl, with the appropriate $C_{1-6}$ alkanol e.g. methanol under conventional esterification conditions, and the resulting ester reacted with hydrazine at elevated temperature to give the acid hydrazide. The acid hydrazide may then be cyclised by condensation with a suitable derivative of the appropriate $C_{1-3}$ alkanoic acid $RCO_2H$, e.g. a trialkyl orthoester, such as the triethyl ortho-ester, the acid derivative acting as the solvent, at elevated temperature.

When Z represents 5-(H or $C_{1-2}$alkyl)-1,3,4-thiadiazol-2-yl a Z' acid hydrazide may be reacted with a suitable acylating agent such as methyl formate or an acetyl or propionyl halide to give a diacyl hydrazide group, $-CONHNHCOR$ which can be cyclised using phosphorus pentasulphide. The cyclisation is preferably carried out in the absence of solvent with the nitrogen of the azabicycle protected as the hydrochloride salt.

When Z represents 1,3-oxazol-2-yl, the conversion may be effected by reaction of a Z' aminocarbonyl group with vinylene carbonate at elevated temperature in the presence of a strong acid such as polyphosphoric acid, which may also function as the solvent.

When Z represents 5-(H or $C_{1-2}$alkyl)-1,3-oxazol-2-yl, a Z' carboxy group may first be converted to the carboxylic acid chloride and then reacted with a compound of formula $NH_2CH_2CR(OR')_2$, or the Z' carboxy group may be reacted directly with the compound of formula $NH_2CH_2CR(OR')_2$ in the presence of a condensing agent such as dicyclohexylcarbodiimide or a chloroformate ester such as ethyl chloroformate, to give a group $CONHCH_2C(OR')_2R$; which may be cyclised using a suitable dehydrating agent such as polyphosphoric acid, phosphorus oxychloride, phosphorus pentachloride, sulphuric acid or sulphuryl chloride, preferably polyphosphoric acid.

A Z 5-(H or $C_{1-2}$alkyl)-1,3-thiazol-2-yl group may be obtained by cyclisation of a Z'—$CONHCH_2C(OR')_2R$ group using phosphorus pentasulphide. The reaction is preferably carried out in the absence of solvent with the nitrogen of the azabicycle protected as the hydrochloride salt.

1,3-Oxazol-2-yl groups 4-methyl-substituted may be provided by the cyclisation of a Z' aminocarbonyl group with propargyl alcohol or acetate ester thereof, in the presence of a dehydrating agent such as polyphosphoric acid using a catalyst such as $HgSO_4$, at elevated temperature.

Alternative routes to optionally 4-substituted 1,3-oxazol-2-yl groups include:

i) the condensation of a Z' aminocarbonyl group with the appropriate compound $BrCH_2COR$ at elevated temperature; or ii) the reaction of a Z' carboxy group under basic conditions with the appropriate compound $BrCH_2COR$ to give a group $-COOCH_2COR$ which may be cyclised with ammonium chloride.

Where R is hydrogen the aldehyde is preferably protected as an acetal.

During the reaction (i) above, the nitrogen atom of the azabicyclic moiety may require protection.

When Z is 4-(H or $C_{1-2}$alkyl)-1,3-thiazol-2-yl a Z' aminothiocarbonyl group may be reacted with the appropriate α-halo acyl compound such as $BrCH_2COCH_3$ as indicated for the corresponding 1,3-oxazole.

1,3-Oxazol-4-yl groups optionally 2-substituted may be provided by reacting a bromomethylcarbonyl group with an appropriate $C_{1-3}$ alkanoic acid amide. Preferably, the reaction with acetamide is carried out at elevated temperature and the reaction with formamide is carried out in sulphuric acid.

An unsubstituted 1,3-oxazol-4-yl group may alternatively be obtained by treatment of a Z'—$CH_2N=C$ group with a formate ester such as methyl formate after deprotonation with a strong base such as n-butyl lithium or potassium t-butoxide.

When Z represents 3-(H or $C_{1-2}$alkyl)-1,2-oxazol-5-yl, the reaction of a Z' $CH_3CO$ group may be carried out at depressed temperature with ethyl formate, acetate or propionate in a suitable solvent such as toluene, under basic conditions such as sodium hydride and catalytic ethanol, followed by reflux, to yield the sodium salt of the resulting dicarbonyl compound. Cyclisation at ambient temperature with an aminating agent such as hydroxylamine-O-sulphonic acid in a dry solvent such as methanol, ethanol or diglyme, preferably in the presence of an acid such as sulphuric acid, p-toluene sulphonic acid or potassium hydrogen sulphate to minimise amination of the azabicycle, yields a compound of formula (I).

Alternatively, the dicarbonyl compound sodium salt may be treated prior to the cyclisation step with dimethylamine in ethanol in the presence of glacial acetic acid at ambient temperature to give the vinylogous amide which may be cyclised as described above.

When Z represents an optionally 5-substituted 1,2-oxazol-3-yl group, a Z'—C≡N+—O− nitrile oxide group may be reacted with an olefin of the structure R-C(W)=CH$_2$, where W is halo such as chloro, OCOCH$_3$ or OSi(CH$_3$)$_3$. The highly reactive nitrile oxide may conveniently be generated in situ from an appropriate Z' halo oxime —C(Br)=NOH by treatment with a base such as triethylamine in a solvent such as N,N-dimethylformamide. The halo oxime is prepared by treatment of a Z'—CH=NOH oxime group with N-bromosuccinimide in N,N-dimethylformamide at ambient temperature, the azabicyclic being in the form of the hydrochloride salt. The Z"—CH=NOH oxime group may be prepared from a Z'—CHO group by reaction with hydroxylamine hydrochloride in a solvent such as methanol.

When Z represents a 2-(H or methyl)-1,3-oxazol-5-yl group, a Z'—COCH$_2$Br group may be converted to —COCH$_2$NH$_2$ by treatment with NaN$_3$ in acetone or N,N-dimethylformamide followed by hydrogenation over a Pd/C catalyst in ethanolic HCl, or by treatment with hexamethylene tetramine followed by hydrolysis in methanolic HCl.

The —COCH$_2$NH$_2$ group may then be acylated with the appropriate derivative of formic acid such as acetic-formic anhydride or acetic acid such as the anhydride or chloride to yield an acyl amino ketone which can be cyclised using a suitable dehydrating agent such as polyphosphoric acid, sulphuric acid or phosphorous pentachloride at elevated temperature.

Alternatively, a Z'—CHO group may be treated with p-toluene sulphonylmethyl isocyanide and anhydrous potassium carbonate in methanol under reflux followed by heating the 4-methoxyoxazoline product with polyphosphoric acid to afford a Z 1,3-oxazol-5-yl group.

When Z represents 2-furyl, a Z" CHO group may be treated with a reactive derivative of propanal such as the 3-tosyl derivative and in which the carbonyl group is preferably protected as a cyclic acetal (X):

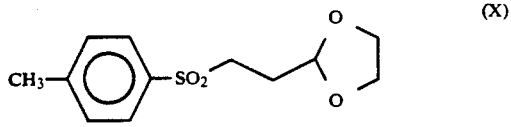

prepared by reaction of sodium 4-methylphenylsulphinate with 2-(2-bromoethyl)-1,3-dioxolane in dimethyl formamide at ambient temperature. The reaction of the compound of formula (X) with the Z'—CHO group in an inert solvent such as tetrahydrofuran in the presence of a base such as n-butyl lithium, initially at low temperature, rising to ambient, yields a compound of formula (XI):

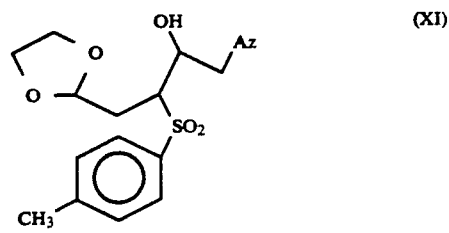

in which A$_z$ represents the azabicyclic moiety, which may be cyclised at elevated temperature in the presence of an acid such as glacial acetic acid, which may also function as the solvent.

Alkyl-substituted 2-furyl groups may be obtained analogously using the appropriately substituted analogue of the compound of formula (X) prepared from the corresponding ketone or aldehyde.

In an alternative procedure to compounds of formula (I) where Z represents a 2- or 3-furyl group, an A' formyl group may be treated with a furan derivative lithiated at the 2- or 3-position, prepared by reaction of a 2-or 3-bromofuran with n-butyllithium in an inert solvent such as diethyl ether at reduced temperature, followed by reduction of the resulting secondary alcohol using triethylsilane in acetonitrile in the presence of a Lewis acid such as stannic chloride or boron trifluoride etherate.

A Z 1,3-thiazol-5-yl group may be obtained by dehydrating and cyclising the corresponding acyl amino ketone using phosphorous pentasulphide at elevated temperature.

Optionally 3-substituted 1,2-thiazol-5-yl groups may be prepared from the corresponding 1,2-oxazolyl group by ring opening effected by treatment with a reducing agent such as Raney nickel and hydrogen in a suitable solvent such as methanol or ethanol to yield a vinylogous amide which may be cyclised using phosphorous pentasulphide in the presence of a suitable oxidising agent such as sulphur or chloranil in a solvent such as toluene at elevated temperature.

Compounds of formula (1) in which Q contains a sulphur atom in place of oxygen may be prepared analogously. A sulphur-containing group Z' is obtained by treatment of a carbonyl-containing group Z' with either phosphorus pentasulphide or with Lawesson's reagent (S.Scheibye, B.S. Pederson and S.O. Lawesson, Bull. Soc. Chim. Belg., 1978, 87(3), 229). The resulting sulphur-containing group Z' may then be converted to the required sulphur-containing group Z analogously to the conversion of carbonyl-containing groups. Where the thiolating agent is phosphorus pentasulphide, this may also effect cyclisation.

Interconversion of carbon substituents R$_1$, R$_2$ and R$_3$ within a group Z may be carried out conventionally. Thus an amino group may be converted to chloro, or —NHNH$_2$, via a diazonium intermediate. Similarly a chloro substituent may be converted by reaction with a nucleophile such as methoxide; and alkoxycarbonyl groups may be converted, via carboxy, to an amino substituent.

Where applicable, an endo isomer may be obtained by epimerisation of a corresponding exo isomer, the epimerisation reaction being effected by standard procedures at any convenient stage in the process but preferably before the introduction of the group Y.

In the above description, R represents H, methyl or ethyl as appropriate and R' represents C$_{1-6}$ alkyl such as methyl or ethyl or two R' groups together represent C$_{2-6}$ polymethylene such as ethylene.

Compounds of formula (II) may be prepared conventionally.

Where A is C$_{1-4}$ alkoxycarbonyl, B is (CH$_2$)$_j$L$_1$ and R$_5$ is hydrogen or an N-protecting group, the compound of formula (II) may be prepared by treating a compound of formula (XII):

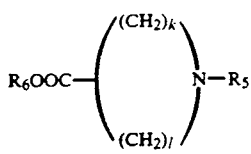

where $R_6$ is $C_{1-4}$ alkyl and the remaining variables are as previously defined, with lithium diisopropylamide, prepared in situ from diisopropylamine and n-butyllithium followed by reaction with a compound $L_5(CH_2)_jL_1$ where $L_5$ is a leaving group, in an inert solvent such as ether at depressed to elevated temperature. Both $L_1$ and $L_5$ are suitably bromo.

Where A and $L_1$ together represent —COO— and j is 2, the compound of formula (II) may be prepared by reacting the compound of formula (XII), treated with lithium diisopropylamide as before, with ethylene oxide in an inert solvent such as ether at depressed to elevated temperature.

Alternatively, the compound of formula (II) where A and $L_1$ together represent —COO, j is 2, k is 2 and l is 1 may be prepared by a 1,3-dipolarcyclo addition reaction which involves reacting a compound of formula (XIII):

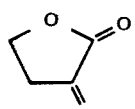

with a compound of formula (XIV):

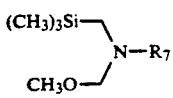

in which $R_7$ is an N-protecting group, in the presence of a catalytic amount of trifluoroacetic acid.

Where A is an electron withdrawing group such as $C_{1-4}$ alkoxycarbonyl, B is hydrogen and $R_5$ is $(CH_2)_jL_2$, the compound of formula (II) may be prepared by reacting the compound of formula (XII) where R5 is hydrogen with a compound $L_5(CH_2)_jL_2$ where $L_5$ is as previously defined, in a solvent such as acetone in the presence of a base such as potassium carbonate. The leaving group $L_5$ is preferably bromo and $L_2$ is preferably chloro.

Compounds of formulae (XII) are known compounds or may be prepared by analogous methods to those for preparing known compounds. The compound of formula (XII) where k is 2, l is 1 and $R_5$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Intermediates of formulae (III) and (IV) are known compounds (e.g. as described in EP-A-0094742 or EP-A-0261763) or may be prepared analogously.

Intermediates of formula (III) where A' and $L_3$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Intermediates of formula (III) where $L_3$ is a leaving group are described in, for example, Spry et al., J. Org. Chem., 1969, 34, 3674 and Hasse et al., Chem. Ber., 1960, 93, 1686.

Intermediates of formula (IV) are described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Compounds of formulae (XIII) and (XIV) may be prepared conventionally. Thus, a compound of formula (XIII) may be obtained by the reaction of γ-butyrolactone with ethyl formate in the presence of base such as sodium hydride followed by reaction of the resulting formyl derivative (as the enol salt) with formaldehyde. A compound of formula (XIV) may be obtained by the reaction of the primary amine $R_7NH_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the following descriptions illustrate the preparation of intermediates thereto.

DESCRIPTION 1

(±) exo 3-Ethoxycarbonyl-1-azabicyclo[2.2.1]heptane
(D1)

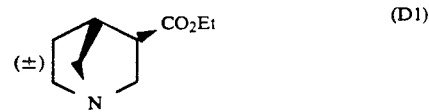

(±) exo Ethyl 1-benzyl-1-azoniabicyclo[2.2.1]hept-3-ylcarboxylate bromide (EP A 0257741 Description 9) (54 g, 0.16 mole) was dissolved in ethanol (400 ml) and hydrogenated over 10% Pd-C (8.5 g) at atmospheric pressure and 25° C. After 2 h the solution was filtered and concentrated in vacuo to leave a gum. This was partitioned between chloroform and saturated aqueous potassium carbonate solution and the organic phase separated, dried (Na₂SO₄) and concentrated in vacuo to leave a gum. This gum was distilled to give the title compound (D1) as a colourless oil (23 g, 85%) b.p. 150° C. at 0.5 mmHg.

¹H Nmr (CDCl₃) δ: 1.10–1.20 (1H,m), 1.25 (3H,t,J=7Hz), 1.54–1.67 (1H,m), 2.15–2.25 (1H,m), 2.28–2.35 (1H,m), 2.38–2.50 (1H,m), 2.60–2.67 (1H,m), 2.70–2.90 (3H,m), 2.93–3.03 (1H,m), 4.13 (2H,q,J=7Hz).

DESCRIPTION 2

(±) exo 3-Methoxycarbonylmethyl-1-azabicyclo[2.2.1]heptane
(D2)

(±) exo 3-Ethoxycarbonyl-1-azabicyclo[2.2.1]heptane (D1) 2g, 12mmol) was heated under reflux in 5N hydrochloric acid (100ml) for 1.5h. The reaction mixture was then concentrated in vacuo to a gum which was dissolved in thionyl chloride (50ml) and heated under reflux for 0.5h. The reaction mixture was then concentrated to a gum, dry toluene (20ml) added and the mixture re-evaporated to remove the last traces of thionyl chloride. The residue on evaporation was dissolved in dry dichloromethane (50ml) and added under dry nitrogen to a solution of diazomethane in dry ether (100mmol in 150ml) at 0° C. with continuous stirring over a period of 15 mins (the ether solution of diazomethane had been pre-dried by stirring with crushed potassium hydroxide pellets for 1h at 0° C.). When the addition was complete the solvents were removed in vacuo at approx. 10° C. and the residue partitioned between chloroform and saturated aqueous potassium carbonate solution. The organic phase was separated and concentrated in vacuo to a gum. The gum was dissolved in methanol (20ml) and treated with freshly prepared silver oxide. (Silver nitrate (1g) in water (10ml) was added to a slight excess of aqueous potassium hydroxide. The precipitate was collected by filtration and washed successively with methanol and ether). The methanol slurry of silver oxide was heated to reflux for 0.5h. The reaction mixture was then filtered through celite and concentrated in vacuo to a gum. The residue was then chromatographed on silica in a gradient of 10–20% methanol in chloroform. Elution with 20% methanol in chloroform afforded a colourless oil which was distilled on a Kugelrohr to afford the title compound (110mg) b.p. 150° C. at 0.1mmHg ¹H NMR (CDCl₃), δ: 1.15 (1H, m, 5H); 1.6 (1H, m, 5H); 1.8 (1H, m, 3H); 2.1 and 2.25 (2H, m, 8H); 2.25 (1H, m, 4H); 2.3 and 2.8 (2H, m, 2H); 2.45 and 2.8 (2H, m, 6H); 3.62 (1H, s, OMe);

¹³C NMR (CDCl₃) δ: 30 CH₂; 39 CH₃; 39 CH₂; 41 CH; 51 CH; 53 CH₂; 57 CH₂, 62 CH₂, 173 C.

DESCRIPTION 2 (ALTERNATIVE PROCEDURE)

(±) exo 3-Methoxycarbonylmethyl-1-azabicyclo[2.2.1]heptane (D2)

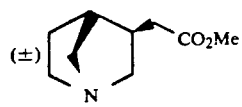

(±) E(3-Ethoxycarbonylmethylene)-1-azabicyclo-[2.2.1]heptane oxalate salt (D5) (2g, 0.007 mol) in methanol (50ml, Ar grade) was added to magnesium metal turnings (4g) under an atmosphere of nitrogen. A crystal of iodine was added and the mixture was warmed to 40° C. until reaction began. After initiation the highly exothermic reaction was placed in a bath of iced water and left to reflux under its own heat of reaction until all the magnesium had been consumed. The reaction was quenched with acetic acid and concentrated in vacuo to leave a solid residue. The residue was basified with saturated aqueous potassium carbonate and partitioned with chloroform. The mixture was filtered through celite and the organic layer was separated, dried (Na₂SO₄) and concentrated in vacuo to afford a pale brown oil comprising a crude 4:1 mixture of endo:exo isomers of the title compound in stoichiometric yield. The crude product was chromatographed on alumina in a gradient of 4 to 10% methanol in ethyl acetate. Elution with 6% methanol in ethyl acetate afforded the title compound (D2) as a colourless oil (150mg, 0.89 mmol, 12%).

¹³C NMR CDCl₃ δ: 30.5, 38.9 (two carbons superimposed), 41.6, 51.3, 53.5, 57.2, 61.9, 173.

Elution with 10% methanol in ethyl acetate afforded the endo isomer (830mg, 0.0049 mol) as a colourless oil.

DESCRIPTION 3

(±) 3-Ethoxycarbonylmethyl-1-azabicyclo[2.2.2]octane (D3)

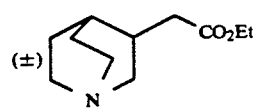

A solution of E,Z-3-carboethoxymethylene-1-azabicyclo[2.2.2]octane* (6.0g, 0.031mol) was hydrogenated in ethanol (250ml) over 10% Pd/C catalyst (770mg) at 150 psi and 45° C. with rocking for 24h. The catalyst was filtered off under nitrogen using celite and the organic filtrate was evaporated to dryness under reduced pressure. The resulting pale yellow oil was purified by Kugelröhr distillation (120° C. at 01.mmHg) to yield the title compound as a clear oil (6.01g, 98%).

¹H NMR (270MHz, CDCl₃) δ: 1.26 (3H, t, Et-CH₃); 1.47 (1H, m); 1.69 (4H, bm); 2.17 (1H, m); 2.41 (3H, m); 2.86 (4H, bm); 3.20 (1H, dd, 3-H); 4.14 (2H, q, Et-CH₂).

IR (NaCl plate) 1715cm⁻¹

MS C₁₁H₁₉NO₂, M⁺found 197.1415, required 197.1411.

*L.N. Yakhontov, L.I. Mastafanova and M.V. Rubstov, Zh. Obshch. Khim., 1963, 33, (10), 3211–14; (C.A. 1964, 60, 4109e).

DESCRIPTION 4

(±) 3-Aminocarbonylmethyl-1-azabicyclo[2.2.2]octane (D4)

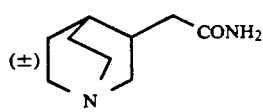

E,Z-3-Carboethoxymethylene-1-azabicyclo[2.2.2]octane (3.0g, 0.0154mol) was stirred with concentrated ammonia solution (125ml) in a sealed flask for 5 days, after which a further portion of concentrated ammonia solution (70ml) was added and the mixture stirred at room temperature for a further three weeks. The ammonia solution was then saturated with solid potassium carbonate and extracted with CHCl₃ (3×500ml).

The organic extracts were dried (Na₂SO₄), filtered and evaporated to dryness under reduced pressure to yield a white solid (2.53g, 99%). The unsaturated amide (2.53g, 0.0152mol) was dissolved in EtOH (20ml), and glacial acetic acid (5ml) and 5% Pt-C catalyst (440mg) added under nitrogen. The mixture was hydrogenated overnight at 150 psi and 40° C. with rocking. The suspension was then filtered under nitrogen through celite and the filtrate evaporated to dryness under reduced pressure. The residue was dissolved in saturated aqeuous potassium carbonate solution, extracted with CHCl₃ (3×250ml) and the organic extracts dried (Na₂SO₄). The organic solution was filtered and evaporated to dryness under reduced pressure to yield a yellow oil which was purified by column chromatography (neutral Al₂O₃ eluting with 2–10% MeOH/CHCl₃) to yield the title compound (1.57g, 61%) as a pale yellow oil.

¹H NMR (270MHz, CDCl₃) δ: 1.47 (1H, m); 1.66 (4H, m); 2.18 (1H, m); 2.41 (3H. bm): 2.83 (4H. bm): 3.18 (1H, dd. 3-H); 5.68 (bs, NH₂).

DESCRIPTION 5

(±) E(3-Ethoxycarbonylmethylene)-1-azabicyclo-[2.2.1.]heptane oxalate salt (D5)

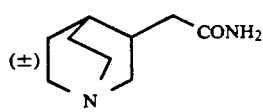

Triethylphosphono acetate (2.69g, 0.012 mole) in dry DMF (10ml) was treated with potassium butoxide (1.59g, 0.013 mole) at 0° C. with continuous stirring under an atmosphere of nitrogen. After 30 minutes 1- azabicyclo[2.2.1]heptane-3-one[1] (1.11g, 0.01 mole) in DMF (10ml) was added at 0° C. and the stirred solution allowed to warm to room temperature over a period of 30 min. After standing at room temperature for 1h the reaction was neutralised with acetic acid and concentrated in vacuo to a gum. The gum was then partitioned between aqueous potassium carbonate and chloroform. The chloroform solution was separated and concentrated in vacuo to a gum. Kugelröhr distillation in vacuo afforded a colourless oil b.pt 200° C. at 0.5mm. The oil was dissolved in ether (20ml) and treated with oxalic acid (900mg) in methanol (2ml). The title compound oxalate salt (D5) slowly crystallised out. Recrystallisation from methanol ether afforded the pure title compound free from the Z isomer as needles (D5) (2.13g; 78%). m.p. 140-150° C.

[1]Douglas O. Spry and Herbert S. Araron, J.O.C. 34. 3674 (1969)

$^1$H NMR DMSO δ: 1.30 (3H, t, J=9Hz, CH$_3$), 1.65-1.75 and 2.25-2.4 (each 1H, m, 5-CH$_2$); 3.25-3.7 (5H, m, 4-CH, 6-CH$_2$, 7-CH$_2$); 4.15-4.25 (2H, q, J=9Hz, CH$_2$CH$_3$); 4.35 (2H, m, 2-CH$_2$); 6.12 (1H, s, CH=C).

DESCRIPTION 6

(±) endo 3-Ethoxycarbonylmethyl-1-azabicyclo[2.2.1]heptane (D6)

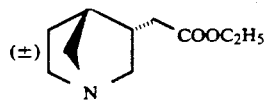

(±) E(3-Ethoxycarbonylmethylene)-1-azabicyclo[2.2.1]heptane oxalate salt (350mg, 0.00125 moles) (D5) was dissolved in ethanol (25ml) and treated with 10% palladium on charcoal (500mg) and stirred under an atmosphere of hydrogen until TLC 20% methanol ethyl acetate indicated complete reduction (24h). The reaction was then filtered through celite and concentrated in vacuo to a gum. The gum was partitioned between chloroform and saturated aqueous potassium carbonate solution. The organic phase was separated and concentrated in vacuo to a gum which was distilled in vacuo to afford (±) endo 3-ethoxycarbonylmethyl-1-azabicyclo[2.2.1]heptane (D6) (140mg, 0.000076 moles, 60%) Bpt 160° C. at 0.1mm containing 10% of the exo isomer.

$^1$H NMR (CDCl$_3$) δ: 1.27 (3H, t, J=8Hz), 1.4-1.55 (2H, m), 1.87-1.96 (1H, m), 2.27-2.58 (7H, m), 2.7-2.9 (1H, m), 3.0-3.15 (1H, m), 4.07-4.2 (2H, q, J=8Hz).

$^{13}$C NMR (CDCl$_3$) (endo isomer) δ: 14.4, CH$_3$; 23.6, CH$_2$; 36.2, CH$_2$; 37.4, CH; 41.16, CH; 55.0, CH$_2$; 60.7, CH$_2$; 60.75, CH$_2$; 61.5, CH$_2$; 173.4, C.

DESCRIPTION 7

(±) endo 3-(N-methyl-N-methoxyaminocarbonylmethyl)-1-azabicyclo[2.2.1]heptane (D7)

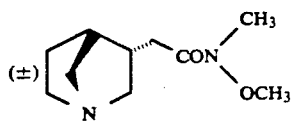

(±) endo 3-(Ethoxycarbonylmethyl)-1-azabicyclo[2.2.1]heptane (D6) (1.15g, 0.0065 moles) was dissolved in concentrated hydrochloric acid (15ml) and water (6 ml) and the mixture was heated under reflux for 2h. The reaction was concentrated in vacuo to leave a brown gum which was azeotroped twice with dry toluene to remove last traces of water. The dry gum was treated with thionyl chloride (11ml) and heated under reflux for 5 mins. Thionyl chloride was removed in vacuo and the residual oil azeotroped three times with dry toluene to afford the acid chloride. To the dry acid chloride in ethanol free chloroform (40ml) was added N,O,dimethyl hydroxylamine hydrochloride (0.644g, 0.0071 moles) under an atmosphere of nitrogen. The mixture was cooled to −60° C. and pyridine (5ml) added dropwise to the stirred solution which was then allowed to warm to room temperature over 2 hours. The reaction mixture was evaporated in vacuo to yield a viscous brown oil which was partitioned between saturated aqueous potassium carbonate and chloroform. The organic phase was separated, dried (Na$_2$SO$_4$) and concentrated in vacuo to afford a brown oil which was distilled on a Kugelröhr to yield the title compound as a colourless oil (0.92g, 0.0046 moles, 71%) b.p. 175° C. at 0.7mmHg. Containing 10% of the exo isomer by Nmr.

$^1$H NMR (CDCl$_3$) δ: 1.37-1.66 (2H, m), 1.8-1.98 (1H, m), 2.21-2.7 (7H, m), 2.7-2.9 (1H, m), 3.15 (1H, m), 3.19 (3H, s), 3.68 (3H, s).

DESCRIPTION 8

(±) 1-Azabicyclo[3.2.1]oct-5-yl-N-methoxy-N-methylcarboxamide (D8)

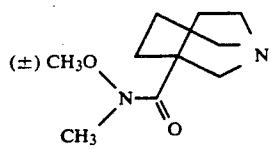

(±) Ethyl 1-azabicyclo[3.2.1]oct-5-ylcarboxylate (Example 7 of EP 0287356, 5g, 0.027mole) in hydrochloric acid (5N, 150ml) was heated under reflux for 1.5h. The reaction was then concentrated in vacuo to a hygroscopic solid which was dissolved in thionyl chloride (100ml) and heated under reflux for 0.5h. The mixture was then concentrated in vacuo to a gum, which was freed from excess thionyl chloride by co-evaporation with toluene. The residue was dissolved in absolute chloroform (100ml) and treated with N,O-dimethylhydroxylamine hydrochloride (2.92g, 0.030 mole) After cooling to 0° C. pyridine (10.9ml, 0.135 mole) was added dropwise. The reaction was allowed to warm to room temperature and stirred for 1h. The reaction mixture was poured into saturated aqueous potassium carbonate solution (100ml) and the mixture was extracted with chloroform (4×100ml). The combined organic extracts were dried (Na$_2$SO$_4$) and evaporated to give an oil which was distilled in vacuo to afford the title compound (D8) (3.77g, 69%) b.p. 60° C. at 0.5 mmHg.

$^1$H-Nmr (CDCl$_3$) δ: 1.47 (1H, m), 1.68-2.13 (7H, m), 2.78-3.15 (6H, m), 3.17 (3H, s), 3.67 (3H, s).

DESCRIPTION 9

(±) 1-Azabicyclo[3.2.1]oct-5-yl carboxaldehyde (D9)

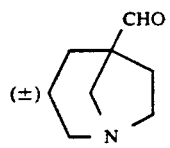

(±) 1-Azabicyclo[3.2.1]oct-5-yl-N-methoxy-N-methyl carboxamide (D8) (10g, 0.05 mole) in dry THF (250ml) was treated with diisobutyl aluminium hydride (43ml of a 1.5M solution in toluene 0.065 mole) at −60° C. The reaction mixture was allowed to warm to −20° C. over a period of 1.5h. The reaction mixture was cooled to −60° C. and poured into 5N hydrochloric acid at −20° C. The reaction mixture was concentrated in vacuo to remove excess tetrahydrofuran and then partitioned between saturated aqueous potassium carbonate and chloroform. The organic phase was separated and concentrated in vacuo to a gum. Kugelröhr distillation afforded the title compound b.p. 140–150 at 0.5mm (D9) (5.5g, 0.0395 mole, 80%).

$^1$H NMR δ: 1.5–2.2 (6H, m), 2.7–3.2 (6H, m), 9.55 (1H, s).

DESCRIPTION 10

(±) 5-Cyanomethyl-1-azabicyclo[3.2.1]octane (D10)

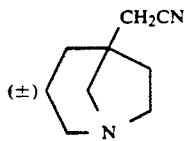

A solution of p-Toluenesulphonylmethyl isocyanide (4.12g, 0.023 mole) in dry 1,2-dimethoxyethane was added slowly to a stirred suspension of potassium t-butoxide (5.15g, 0.042 mole) in 1,2-dimethoxyethane (30ml) kept at −60° C. under an atmosphere of nitrogen. (±) 1-Azabicyclo[3.2.1]oct-5-yl carboxaldehyde (D9) (2.99g, 0.0215 mole) in 1,2-dimethoxyethane (30ml) was added dropwise to the mixture at −60° C. The reaction was stirred at −60° C. for 1.5h and then for a further 1h at room temperature. Methanol (50ml) was added and the reaction was then heated under reflux for 15 min. Solvent was removed in vacuo and the residue was partitioned between saturated aqueous potassium carbonate and chloroform. The organic phase was separated, dried (Na$_2$SO$_4$) and concentrated in vacuo. The crude material was distilled on a Kugelröhr to afford the title compound (D10) (2.16g, 0.014 mole, 67%).

$^1$H NMR (CDCl$_3$) δ: 1.5–1.87 (6H, m, together 3-CH$_2$, 4-CH$_2$, 8-CH$_2$) 2.35 (2H, s, 9-CH$_2$), 2.5–2.9 (5H, m) and 2.95–3.07 (1H, m) together (2-CH$_2$, 6-CH$_2$, 7-CH$_2$).

$^{13}$C NMR (CDCl$_3$) δ: 2.0 (CH$_2$), 26 (CH$_2$), 35.8 (2×CH$_2$ superimposed), 40.09 (tertiary C, C-5), 52 (CH$_2$), 54.4 (CH$_2$), 64.3 (CH$_2$), 117.8 (C-10).

DESCRIPTION 11

(±) 5-Methoxycarbonylmethyl-1-azabicyclo[3.2.1]octane (D11)

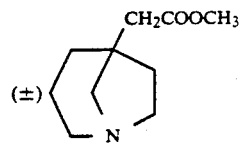

(±) 5-Cyanomethyl-1-azabicyclo[3.2.1]octane (D10, 2.16g, 0.0144 mole) was dissolved in concentrated hydrochloric acid (55ml) and heated under reflux for 2h. The reaction mixture was evaporated to dryness and the residue dissolved in methanol saturated with hydrogen chloride gas. After 2 hours at 20° C., the reaction mixture was concentrated in vacuo to a gum which was partitioned between saturated aqueous potassium carbonate and chloroform. The organic phase was separated, dried (Na$_2$SO$_4$) and concentrated in vacuo to yield a crude oil. The oil was distilled on a Kugelröhr to afford the title compound (D11) as a colourless oil (1.74g, 0.0095 mole, 66%).

$^1$H NMR, δ: 1.37–1.88 (6H, m), 2.38 (2H, s, 9-CH$_2$), 2.52–3.08 (6H, m), 3.67 (3H, s, CH$_3$).

$^{13}$C NMR δ: 20, 35.5, 36, 41.2, 42.9, 51.2, 51.9, 54.5, 65, 172.1.

DESCRIPTION 12

(±) endo 3-(Aminocarbonylmethyl)-1-azabicyclo[2.2.1]heptane (D12)

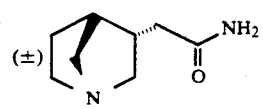

(±) E(3-Ethoxycarbonylmethylene)-1-azabicyclo[2.2.1]heptane oxalate salt (D5) (10.83g, 0.04 mole) in ethanol (200ml) was stirred with 10% palladium on charcoal (1.5g) at 40° C. under an atmosphere of hydrogen for 4h. The solution was then filtered through celite and concentrated in vacuo to a gum which was partitioned between chloroform and saturated aqueous potassium carbonate solution, the organic phase was separated, dried over sodium sulphate and concentrated in vacuo to a gum (6.74g). This material was dissolved in concentrated hydrochloric acid (50ml) and water (20ml) and heated under reflux for 7h. The reaction was concentrated in vacuo to a gum and azeotroped with toluene to remove the last traces of water. The residue was treated with thionyl chloride (50ml) and heated under reflux for 15 min when a homogenous solution was obtained. The solution was then concentrated in vacuo to a gum which was azeotroped three times with toluene to remove the last traces of thionyl chloride. The residue was dissolved in dry dichloromethane (200ml) and the solution cooled to −50° C. under an atmosphere of nitrogen. A saturated solution of ammonia in dichloromethane (500ml) was added slowly so as to keep the temperature below −40° C. The reaction was allowed to warm to 20° C. over a period of 4h with stirring. Saturated aqueous potassium carbonate solution was added and the organic phase separated, dried over sodium sulphate and concentrated in vacuo to a gum. The gum was recrystallised from THF/ether to afford the title compound (D12) (4,36g, 0.028 mole, 70%). M.pt =60-65° C. containing 10% of the exo isomer.

DESCRIPTION 13

(±) endo 3-(Cyanomethyl)-1-azabicyclo[2.2.1]heptane (D13)

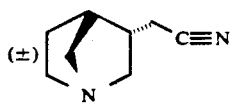

(±) endo 3-Aminocarbonylmethyl-1-azabicyclo[2.2.1]heptane (D12) (4.36g, 0.028 moles) was suspended in dry THF (150ml) and treated with pyridine (5ml, 0.056 moles) and trifluoroacetic anhydride (4.67ml, 0.0308 moles) at room temperature with continuous stirring at such a rate that the temperature did not rise above 30° C. After 1.5h at 25° C. the reaction was treated with water (3ml) and concentrated in vacuo to low volume (40ml). The reaction was then partitioned between chloroform and saturated aqueous potassium carbonate solution. The organic phase was separated, dried over sodium sulphate and concentrated to a brown oil. Kugelröhr distillation afforded the title compound (D13) as a Colourless oil. B.pt. 150°0 C. at 0.1mmHg.

$^1$H NMR (CDCl$_3$) δ: 1.4-1.6 (2H, m), 1.9-2.0 (1H, m), 2.2-2.7 (7H, m), 2.8-2.95 (1H, m), 3.0-3.2 (1H, m)

DESCRIPTION 14

(±) 5-[(Fur-2-yl)hydroxymethyl]-1-azabicyclo[3.2.1]octane (D14)

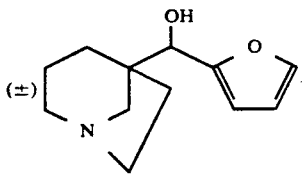

A stirred solution of furan (510mg, 0.0075 mole) in dry ether (30ml) at −40° C. under nitrogen was treated with 1.6M n-butyllithium in hexane (4.2ml, 0.0067 mole) and then allowed to warm to room temperature over 2h. The solution was cooled to −60° C. and treated with a solution of (±) 1-azabicyclo[3.2.1]oct-5-ylcarboxaldehyde (D9, 850mg, 0.0061 mole) in ether (10ml). A white precipitate immediately formed. The mixture was allowed to warm to room temperature over 1h, then treated with saturated potassium carbonate solution (15ml) and extracted with ethyl acetate (2×40ml). The combined extracts were dried (Na$_2$SO$_4$) and concentrated in vacuo to leave an orange oil, which was passed through a short basic alumina column eluting with ethyl acetate to give the title compound (D14) as a pale yellow oil (750mg, 59%).

$^1$H NMR (CDCl$_3$) δ: 1.25-2.10 (6H, m), 2.40-3.00 (6H, m), 4.43 (1H, s), 5.55 (1H, br.s, OH), 6.07-6.37 (2H, m), 7.23-7.33 (1H, m).

DESCRIPTION 15

(±) E/Z 3-Ethoxycarbonylmethylene-1-azabicyclo[3.2.1]octane (D15)

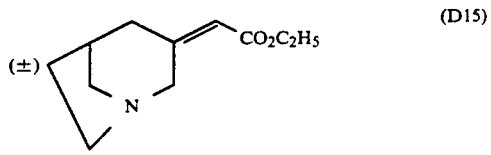

Triethylphosphonoacetate (7.17g, 0.032 mole) in dry dimethylformamide (20ml) was treated with potassium tertiary butoxide (3.9g, 0.035 mole) under an atmosphere of nitrogen for 30 min at 0° C. To this solution was added 1-azabicyclo[3.2.1]octan-3-one* (1.93g, 0.016 mole) in dry dimethylformamide (30ml) and the reaction allowed to warm to room temperature over 4h. The reaction was quenched with acetic acid (5ml), evaporated to dryness in vacuo and the residue partitioned between saturated aqueous potassium carbonate and chloroform. The organic phase was separated, dried (Na$_2$SO$_4$) and concentrated in vacuo to a yellow oil. The oil was chromatographed on silica in a gradient of 20-40% methanol in chloroform. Elution with 30% methanol in chloroform afforded the title compound (D15) (1.05g, 34%) as a viscous oil containing a 3:1 mixture of E/Z isomers.

*D.P. Thill and H.S. Aaron, J. Org. Chem., 1968, 33, 4376.

$^1$H NMR (CDCl$_3$) δ: 1.29 (3H, t), 1.57-1.9 (2H, m), 2.2-2.72 (2H, m), 2.72-3.16 (4H, m), 3.2-3.74 (3H, m), 4.15 (2H, q), 5.73 (1H, s).

$^{13}$C NMR (CDCl$_3$) (major isomer) δ: 31.3 (CH3), 47.4 (C-6), 52.2 (C-5), 53.1, 69.2, 77.0, 77.1, 80.5, 135.2, 173.9, 182.9 (C=O)

DESCRIPTION 16

N-Benzyl-N-[(trimethylsilyl)methyl]amine (D16)

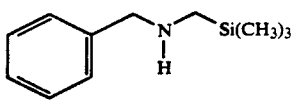

A mixture of chloromethyltrimethylsilane (325g, 370ml, 2.65 mole) and benzylamine (835g, 850ml, 7.78 mole) was heated at 120° C. (oil bath temperature) for 2h. A white solid began appearing after only 10 minutes and a viscous mixture eventually resulted. The reaction mixture was allowed to cool, then basified with potassium carbonate solution and extracted twice with ether. The combined extracts were dried (Na$_2$SO$_4$) and concentrated in vacuo to leave a yellow oil, which was purified by distillation. The excess benzylamine was removed in the first fractions (b.p. 47-62° C. at 2mmHg). The title compound (D16) was obtained as a colourless oil (380g, 74%) b.p. 75-80° C. at 2mmHg.

$^1$H NMR (CDCl$_3$) δ: 0.10 (9H, s), 1.40 (1H, br.s, NH), 2.10 (2H, s), 3.85 (2H, s), 7.27-7.43 (5H, m)

DESCRIPTION 17

N-Benzyl-N-(methoxymethyl)-N-[(trimethylsilyl)methyl]amine (D17)

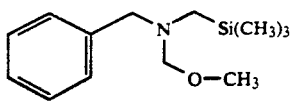
(D17)

A stirred 37% aqueous formaldehyde solution (230g, 215ml, 2.8 mole) was cooled to −5° C. and treated dropwise over 20 minutes with N-benzyl-N-[(trimethylsilyl)methyl]amine (D16, 380g, 1.96 mole), whilst keeping the temperature between −5 and 0° C. After completing the addition, the mixture was treated with methanol (230ml), saturated with potassium carbonate and stirred at room temperature for 2h. The mixture was treated with ether (500ml) and the organic phase separated, dried (K$_2$CO$_3$) and concentrated in vacuo to give a colourless oil (480g), which was about 75% title compound (D17). This material was used in the next stage without purification.

$^1$H NMR (CDCl$_3$) δ: 0.10 (9H,s), 2.23 (2H, s), 3.30 (3H, s), 3.82 (2H, s), 4.05 (2H, s), 7.25–7.40 (5H, m)

DESCRIPTION 18

α-Formyl-γ-butyrolactone sodium salt (D18)

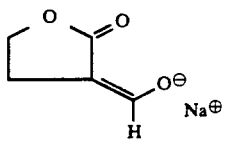
(D18)

A stirred suspension of sodium hydride (300g of 80% oil dispersion, 10 moles) in dry ether (8l) under nitrogen was treated slowly with absolute ethanol (60ml, 1.1 mole), followed immediately by a mixture of ethyl formate (808 ml, 10 moles) and γ-butyrolactone (770ml, 10 moles) over about 1.25h. The rate of addition of the reagents was regulated to give a steady reflux and evolution of hydrogen (about 220l). After completing the addition, the mixture was stirred for a further 0.5h and the solid then filtered off, washed with ether and dried in vacuo to give the title compound (D18) as a white solid (1.32kg, 97%).

DESCRIPTION 19

α-Methylene-γ-butyrolactone (D19)

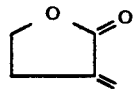
(D19)

A stirred suspension of paraformaldehyde (270g, 9.0 mole) in THF (3.5L) at room temperature in a 20L flask under nitrogen was treated with α-formyl-γ-butyrolactone sodium salt (D18, 270g, 2.0 mole). The mixture was then immediately heated to reflux temperature for 1h. Evolution of a small quantity of gas was observed. The mixture was cooled to around 10° C., treated with saturated aqueous potassium carbonate solution (500ml) and ether (1.5L), and the organic layer separated, dried (Na$_2$SO$_4$) and concentrated in vacuo to leave a pale yellow oil. This material was distilled to give the title compound (D19) as a colourless oil (125g, 64%) b.p. 76–80° C. at 8mmHg.

$^1$H NMR (CDCl$_3$) δ: 2.95–3.03 (2H, m), 4.40 (2H, t, J=7Hz), 5.69 (1H, t, J=3Hz), 6.25 (1H, t, J=3Hz)

DESCRIPTION 20

7-Benzyl-7-aza-2-oxaspiro4.4]nonan-1-one (D20)

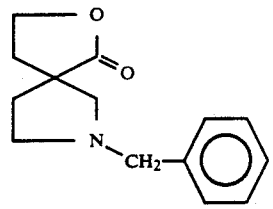
(D20)

A stirred solution of N-benzyl-N-(methoxymethyl)-N-[(trimethylsilyl)methyl]amine (D17, 160g of 75% purity, assume 0.51 mole) and α-methylene-γ-butyrolactone (D19, 50g, 0.51 mole) in dichloromethane (1l) under nitrogen was cooled to 0° C. and then treated with a 1M solution of trifluoroacetic acid in dichloromethane (50ml, 0.05 mole), keeping the temperature below 5° C. The reaction mixture was allowed to warm to room temperature over 2h, then washed with saturated sodium bicarbonate solution. The aqueous wash was extracted with dichloromethane and the organic solutions then combined, washed with brine, dried (Na$_2$SO$_4$) and concentrated in vacuo to leave a pale yellow oil. This was distilled in vacuo to give the title compound (D20) as a colourless oil (96g, 81%) b.p. 160–170° C. at 1mmHg.

$^1$H NMR (CDCl$_3$) δ: 1.77–1.92 (1H, m), 2.15–2.40 (3H, m), 2.48–2.78 (3H, m), 2.85–2.98 (1H, m), 3.55–3.70 (2H, m), 4.10–4.30 (2H, m), 7.15–7.35 (5H, m)

DESCRIPTION 21

Ethyl 1-benzyl-1-azoniabicyclo2.2.1]hept-4-ylcarboxylate bromide (D21)

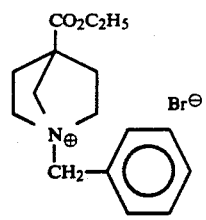
(D21)

A stirred solution of 7-benzyl-7-aza-2-oxaspiro[4.4]-nonan-1-one (D20, 96g, 0.42 mole) in ethanol (150ml) was saturated with hydrogen bromide gas and then left to stand for 18h. The solution was concentrated in vacuo and the residue basified with saturated potassium carbonate solution and extracted with chloroform. The organic extract was dried (Na$_2$SO$_4$) and concentrated in vacuo to leave a pale brown oil. This was treated with ether and the resulting solid filtered off, washed with ether and dried to give the title compound (D21) as a white solid (130g, 91%).

DESCRIPTION 22

Ethyl 1-azabicyclo2.2.11]hect-4-ylcarboxylate hydrobromide salt (D22)

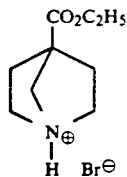

(D22)

A suspension of ethyl 1-benzyl-1-azoniabicyclo[2.2.1-]hept-4-ylcarboxylate bromide (D21, 130g, 0.38 mole) in ethanol (500ml) was hydrogenated over 10% palladium on charcoal catalyst (8g) at atmospheric temperature and pressure for 18h. The catalyst was removed by filtering through celite, washing several times with hot ethanol, and the filtrate concentrated in vacuo to give the title compound (D22) as a crystalline white solid (80.1g, 84%).

$^1$H NMR (CD$_3$OD) δ: 1.3 (3H, t, J=7Hz), 2.0–2.18 (2H, m), 2.3–2.5 (2H, m), 3.35–3.5 (2H, m), 3.45 (2H, s), 3.5–3.7 (2H, m), 4.25 (2H, q, J=7Hz)

DESCRIPTION 23

4-(N-Methyl-N-methoxyaminocarbonyl)-1-azabicyclo[2.2.1]heptane (D23)

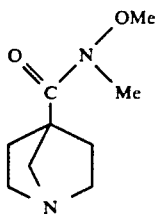

(D23)

Ethyl 1-azabicyclo[2.2.1]hept-4-yl carboxylate hydrobromide salt (D22) (10g, 0.04 moles) was dissolved in concentrated hydrochloric acid (55ml) and water (22ml) and heated under reflux for 16h. The reaction was then concentrated in vacuo and azeotroped once with toluene to afford a colourless solid. This product was suspended in thionyl chloride (80ml) and heated under reflux for 4h when the solution was homogenous. The reaction was then concentrated in vacuo and the residue azeotroped with dry toluene until a crystalline residue was obtained. This material was suspended in dry acetonitrile (150ml) and N,O-dimethyl hydroxylamine hydrochloride (4.4g, 0.045 moles) added. The stirred solution was cooled to −30° C. and pyridine (16ml) added at such a rate that the temperature did not rise above −20° C. The solution was then allowed to warm to room temperature overnight when a homogenous solution was obtained. The solution was then concentrated in vacuo to a gum which was partitioned between chloroform and saturated aqueous potassium carbonate. The organic phase was separated, dried over Na$_2$SO$_4$ and concentrated in vacuo to a gum. Kugelröhr distillation afforded the title compound (D23) (6.48g, 0.035 moles, 88%). B.pt. 150–160 at 2mmHg as a white solid. M.pt. 108–110° C.

$^1$H NMR (CDCl$_3$) δ: 1.6–1.75 (2H, m, 3H, 5H), 1.85–1.95 (2H, m, 3H, 5H), 2.57–2.7 (2H, m, 2H, 6H), 2.75 (2H, s, 7-CH$_2$), 2.95–3.1 (2H, m, 2H, 6H), 3.25 (3H, s, NMe), 3.7 (3H, s, OMe).

$^{13}$C NMR (CDCl$_3$) δ: 33.0, 33.9, 55.5, 55.6, 61.4, 63.0, 175.6

DESCRIPTION 24

4-Formyl-1-azabicyclo[2.2.1]heptane (D24)

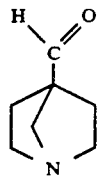

(D24)

4-(N-Methyl-N-methoxyaminocarbonyl)-1-azabicyclo [2.2.1]heptane (D23) (6.48g, 0.035 mole) in dry tetrahydrofuran (100ml) was cooled to −70° C. under an atmosphere of nitrogen (a fine suspension of the amide formed on cooling). To this was added diisobutyl aluminium hydride in hexane (30ml of 1.5M solution, 0.045 mole) and the solution stirred at −70° C. for 1h and then allowed to warm to room temperature over 2h. The reaction was then cooled to −60° C. and poured a well stirred slurry of ice and 5N HCl (40ml). The solution was then basified with excess potassium carbonate and the product recovered by exhaustive extraction with chloroform. The chloroform extract was dried over Na$_2$SO$_4$ sulphate and concentrated in vacuo to a gum. The gum was purified by Kugelröhr distillation to afford the title compound (D24) (4.05g, 0.0324 mole, 93% B.pt 75–85° C. at 0.4mmHg as a colourless oil.

$^1$H NMR (CDCl$_3$) δ: 1.3–1.43 (2H, m, 3H, 5H), 2.0–2.17 (2H, m, 3H, 5H), 2.6–2.75 (2H, m, 2H, 6H), 2.65 (2H, s, 7-CH$_2$), 3.0–3.14 (2H, m, 2H, 6H), 9.95 (1H, s, CHO).

$^{13}$C NMR (CDCl$_3$) δ: 31.8, 55.2, 55.5, 62.7, 202.5

DESCRIPTION 25

4-(Cyanomethyl)-1-azabicyclo[2.2.11]heptane (D25)

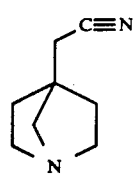

(D25)

Toluene sulphonyl methyl isocyanide (4.29g, 0.022 mole) in dry 1,2 dimethoxyethane (25ml) was added to a stirred suspension of potassium t-butoxide (5.13g, 0.042 mole) in dimethoxyethane (30ml) at −50° C. under an atmosphere of nitrogen. A solution of 4-formyl-1-azabicyclo[2.2.1]heptane (D24) (2.625g, 0.021 mole) in dimethoxyethane (30ml) was added at −50° C. and stirred at this temperature for 1.5h. The solution was then allowed to warm to room temperature and stirred at 25° C. for 1h. Methanol (50ml) was then added and the solution heated under reflux for 15 min. The solution was then concentrated in vacuo to a gum and the residue partitioned between saturated aqueous potassium carbonate and chloroform. The organic phase was separated dried over sodium sulphate and concentrated in vacuo to a gum. Kugelröhr distillation afforded the title compound (D25) (1.8g, 0.0132 mole, 63%) as a colourless oil. B.pt 140° C. at 0.5mmHg.

¹H NMR (CDCl₃) δ: 1.33–1.5 (2H, m, 3H, 5H), 1.6–1.75 (2H, m, 3H, 5H), 2.4 (2H, s, 7-CH₂), 2.6–2.75 (2H, m, 2H, 6H), 2.75 (2H, s, 8-CH₂), 2.95–3.1 (2H, m, 2H, 6H)

DESCRIPTION 26

4-(Ethoxycarbonylmethyl)-1-azabicyclo[2.2.1]heptane (D26)

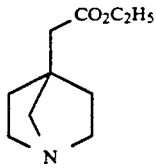

(D26)

4-(Cyanomethyl)-1-azabicyclo[2.2.1]heptane (D25) (0.9g, 0.0062 moles), was dissolved in 5N hydrochloric acid, (25ml) and heated under reflux for 12h. The reaction was then concentrated in vacuo to a gum and dissolved in ethanol (20ml), to which was added concentrated sulphuric acid (1ml) and the solution heated under reflux for 15 min. The solution was then concentrated in vacuo to a gum. Kugelröhr distillation afforded the title compound (D26) (0.85g, 0.00464 mole, 70%) as an oil. B.pt 150° C. at 0.5mmHg.

¹H NMR (CDCl₃) δ: 1.28 (3H, t, J=7Hz, CH₃), 1.33–1.48 (2H, m, 3H, 5H), 1.5–1.75 (2H, m, 3H, 5H), 2.40 (2H, s, 7-CH₂), 2.5–2.7 (2H, m, 2H, 6H), 2.68 (2H, s, 8-CH₂), 2.88–3.1 (2H, m, 2H, 6H), 4.15 (2H, q, J=7Hz, OCH₂).

DESCRIPTION 27

4-(Aminocarbonylmethyl)-1-azabicyclo[2.2.1]heptane (D27)

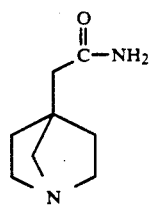

(D27)

4-(Cyanomethyl)-1-azabicyclo[2.2.1]heptane (D25) (0.9g, 0.0066 mole) was heated under reflux with 5N hydrochloric acid (30ml) for 4h and then concentrated in vacuo to a gum. This was azeotroped with toluene to afford the anhydrous acid hydrochloride which was treated with thionyl chloride (20ml) which was heated under reflux for 2h when a homogeneous solution was obtained. The excess thionyl chloride was removed in vacuo and the residue azeotroped with toluene to remove the last traces of thionyl chloride. The residue was dissolved in dichloromethane (50ml) and cooled to −50° C. with stirring. To this was added dichloromethane (100ml) saturated with ammonia at −50° C. and the stirred reaction allowed to warm to 20° C. over 2h. Excess saturated aqueous potassium carbonate solution was added and the organic phase separated, dried over sodium sulphate and concentrated in vacuo to a gum. Crystallisation from methanol/ether afforded the title compound (D27) (400mg, 0.0026 mole, 39%) as needles. M.p. 143–145° C.

¹H NMR ((CD₃)₂SO) δ: 1.1–1.3 (2H, m, 3H, 5H), 1.4–1.58 (2H, m, 3H, 5H), 2.2 (2H, s, 7-CH₂), 2.38 (2H, s, 8-CH₂), 2.35–2.5 (2H, m, 2H, 6H), 2.65–2.8 (2H, m, 2H, 6H), 3.5 (Br s, H₂O), 6.75 (1H, s, NH), 7.3 (1H, s, NH)

DESCRIPTION 28

(±) 3-(N-hydroxy)-carboximidamide methyl]-1-azabicyclo2.2.1]heptane (D28)

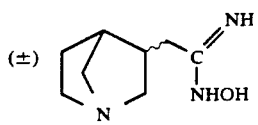

(D28)

Hydroxylamine hydrochloride (1.67g, 0.0236 mole) was added to a solution of sodium (0.552g, 23.6 mole) in methanol (40ml) under nitrogen and the reaction heated under reflux for 15 min whereupon the hydroxylamine hydrochloride had completely dissolved and the resulting sodium chloride had precipitated out. (±) endo 3-(Cyanomethyl)-1-azabicyclo[2.2.1]heptane (D13) (0.8g, 0.0059 mole) in methanol (30ml) was added and the mixture heated under reflux for 48h. The reaction was then concentrated in vacuo to a gum and the residue partitioned between saturated aqueous potassium carbonate (5ml) and water. The organic phase was separated and repeatedly extracted with chloroform. The combined organic extracts were dried over sodium sulphate and concentrated in vacuo to give the title compound as a 10:1 mixture of endo:exo isomers (D28) (0.9g, 0.0053 mole, 90%).

Ir νC≡N 1660cm⁻¹

¹H NMR (CDCl₃) δ: 1.35–1.70 (2H, m), 1.9–2.05 (1H, m), 2.12–2.6 (8H, m), 2.74–2.91 (1H, m), 3.0–3.18 (1H, m), 4.4–4.55 (2H, m).

DESCRIPTION 29

(±) 3-[(N-Acetoxy)-carboximidamide methyl]-1-azabicyclo 2.2.1]heptane (D29)

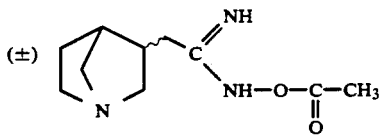

(D29)

(±) 3-[(N-hydroxy)-carboximidamidemethyl]-1-azabicyclo[2.2.1]heptane (D28) (0.37g, 0.0022 mole) in absolute chloroform was cooled to 0° C. and treated with acetyl chloride (0.2g, 0.0026 mole) under nitrogen. The reaction was allowed to warm to room temperature over 1h. The solution was then cooled to 0° C. and treated with saturated aqueous potassium carbonate solution (10ml). The organic layer was separated, the aqueous layer repeatedly extracted with chloroform and the combined organic extracts dried over sodium sulphate and concentrated in vacuo to afford the title compound (as a 10:1 mixture of exo:endo isomers) (D29) (0 42g, 0.002 mole, 91%).

DESCRIPTION 30

(±) Ethyl 1-azabicyclo[2.2.2]oct-3-yl carboxylate (D30)

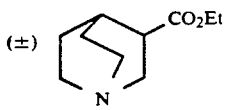

Hydrogen chloride gas was bubbled through a solution of (±) 3-cyano-1-azabicyclo[2.2.2]octane (D1 of EP-0261763) (48.5g, 0.357 moles) in ethanol (300ml) causing the solution to reflux. The mixture was maintained at reflux while hydrogen chloride gas was bubbled through for 3h. The mixture was allowed to cool and then concentrated in vacuo. The residue was partitioned between saturated potassium carbonate solution and chloroform. The organic layer was dried ($Na_2SO_4$) and evaporated to dryness. The residue was distilled to give the title compound (D30) as a colourless liquid (42.5g, 65%) b.p. 100° C. at 1.0mmHg.

$^1$H NMR ($CDCl_3$) δ: 1.25 (3H, t), 1.33–1.50 (1H, m), 1.55–1.72 (3H, m), 2.15–2.21 (1H, m), 2.50–3.10 (6H, m), 3.25–3.38 (1H, m), 4.17 (2H, q).

DESCRIPTION 31

(±) 3-(N-methyl-N-methoxyaminocarbonyl-1-azabicyclo 2.2.2]octane (D31)

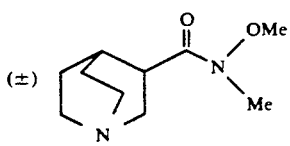

(±) Ethyl 1-azabicyclo[2,2,2]oct-3-yl carbox 80%) b.p. 120° C. at 1.0mmHg.

DESC

DESCRIPTION 32

(±) 3-Formyl-1-azabicyclo[2.2.2]octane (D32)

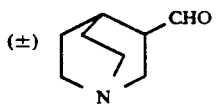

(±) 3-(N-Methyl-N-methoxyaminocarbonyl)-1-azabicyclo[2.2.2]octane (D31) (6.0g, 0.03 moles) was dissolved in dry toluene (250ml) and cooled to −70° C. under a nitrogen atmosphere. Diisobutylaluminium hydride (1.5M solution in toluene (45ml, 0.068 moles) was added dropwise. The reaction was then allowed to warm to room temperature over a period of 2h. Hydrochloric acid (2N, 300ml) was added rapidly with vigorous stirring. The aqueous layer was saturated with potassium carbonate and the mixture extracted with chloroform (3×250ml). The combined extracts were dried ($Na_2SO_4$) and evaporated to dryness. The residue was distilled in a Kugelröhr to yield the title compound (D32) as a colourless oil (3.6g, 85%) b.p. 100° C. at 1.0

$^1$H NMR ($CDCl_3$) δ: 1.39–1.58 (2H, m), 1.62–1.75 (2H, m), 2.29–2.35 (1H, m), 2.50–2.60 (1H, m), 2.72–2.98 (5H, m), 3.30–3.43 (1H, m), 9.80 (1H, s).

DESCRIPTION 33

(±) 3-((1,3-Thiazol-2-yl)hydroxymethyl)-1-azabicyclo[2.2.2]octane (D33)

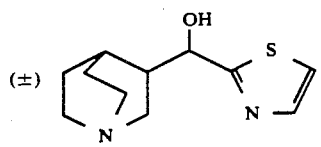

A mixture of (±) 3-formyl-1-azabicyclo[2.2.2]octane (D32) (2 5g, 0.018 moles) and 2-trimethylsilyl-1,3-thiazole (2.7g, 0.017 moles) was stirred together without solvent at room temperature for 3h. The mixture was diluted with tetrahydrofuran (100ml) and then treated with tetrabutylammonium fluoride trihydrate (5.4g, 0.017 moles). After 1h the mixture was concentrated in vacuo and the residue partitioned between saturated potassium carbonate solution and chloroform. The organic layer was dried ($Na_2SO_4$) and evaporated to dryness. The residue was subjected to column chromatography on TLC alumina eluting with 0.5% methanol/chloroform. This gave an oil which was triturated with diethylether/methanol to yield the title compound (D33) as a buff solid (0.5g, 13%).

$^1$H NMR ($CDCl_3$) δ: 1.40–1.72 (3H, m), 1.75–1.92 (1H, m), 2.00–2.20 (2H, m), 2.42–2.53 (1H, m), 2.63–2.89 (5H, m), 4.80 (1H, d), 7.29 (1H, d), 7.69 (1H, d).

DESCRIPTION 34

(±) Z 3((1,3-Thiazol-2-yl)methylene)-1-azabicyclo[2.2.2]octane (D34)

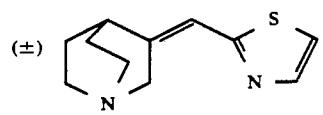

A mixture of (±) 3-((1,3-thiazol-2-yl)hydroxymethyl)-1-azabicyclo[2.2.2]octane (D33) (0 49g, 0.0022 moles) and toluene-4-sulphonic acid monohydrate (1.2g, 0.0063 moles) was heated under reflux in xylene (60ml) for 24h. A 'Dean and Stark' apparatus was used to trap the eliminated water. The mixture was allowed to cool and then concentrated in vacuo. The residue was partitioned between saturated potassium carbonate solution and chloroform. The organic layer was dried ($Na_2SO_4$) and evaporated to dryness. The residue was subjected to column chromatography on silica gel eluting with 0–5% methanol/chloroform. This yielded the title compound (D34) (0.23g, 51%) as a white solid plus a smaller amount of the E isomer.

$^1$H NMR ($CDCl_3$) δ: 1.70–1.92 (4H, m), 2.03–2.11 (1H, m), 2.82–3.09 (4H, m), 3.87 (2H, s), 6.55–6.62 (1H, m), 7.27 (1H, d), 7.79 (1H, d).

EXAMPLE 1

(±) exo 3-[(3-Amino-1,2,4-oxadiazol-5-yl)methyl]-1-azabicyclo[2.2.1]heptane (E1)

Sodium (95mg, 4mmol) was dissolved in ethanol (50ml) and to this was added hydroxy guanidine sulphate hemihydrate (314mg, 1.18mmol) and powdered 4A molecular sieve (1g) under nitrogen at room temperature. To this solution was added (±) exo 3-methoxycarbonylmethyl-1-azabicyclo[2.2.1]heptane (D2) (100mg; 0.59mmol) and the stirred solution heated under reflux for 1.5h. Acetic acid (1ml) was added and the reaction concentrated in vacuo to a gum. The gum was partitioned between chloroform and saturated aqueous potassium carbonate solution. The organic phase was separated, dried ($Na_2SO_4$) and concentrated in vacuo to a solid. A solution in chloroform/ether 1:1 was treated with decolourising charcoal (1g), filtered and concentrated to a gum. The gum was allowed to crystallise from ether to afford the title compound (E1) (26mg, 23%) as needles, m.p. 114–115° C.

$^1$H NMR (CDCl$_3$) δ: 1.18 (1H, m, 5H); 1.60 (1H, m, 5H); 1.90 (1H, m, 3H); 2.3–2.9 (9H); 4.35 (2H, bs, NH2)

$^{13}$C NMR (CDCl$_3$) δ: 30.9, 31.7, 40.6, 41.8, 53.9, 57.6, 62.0, 168, 178.

EXAMPLE 2

(±) 3-[(3-Methyl-1,2,4-oxadiazol-5-yl)methyl]-1-azabicyclo[2.2.2]octane hydrochloride salt (E2)

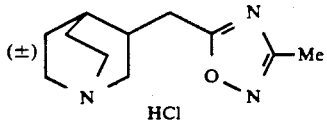

(±) 3-Ethoxycarbonylmethyl-1-azabicyclo[2.2.2]octane (D3) (1.10g, 5.6mmol) was dissolved in concentrated hydrochloric acid (25ml) and heated at reflux with stirring for 2h. The solution was evaporated to dryness under reduced pressure and dried in a vacuum desiccator overnight to yield the acid hydrochloride (1.10g, 96%). The acid hydrochloride (1.10g, 5.35mmol) was suspended in thionyl chloride (20ml) and stirred at room temperature under nitrogen for 60h. The yellow solution was evaporated to dryness under reduced pressure, dried azeotropically with toluene and the resulting orange solid suspended in ethanol-free chloroform. Acetamide oxime (0.580g, 7.8mmol) was added and the mixture heated at reflux for 4h. The mixture was allowed to cool, diluted with water and saturated with solid anhydrous potassium carbonate. The chloroform layer was separated and the aqueous layer re-extracted with chloroform (100ml). The combined organic extracts were then washed with saturated aqueous potassium carbonate solution (100ml) and the organic extracts were then dried ($Na_2SO_4$), filtered and evaporated to dryness under reduced pressure to yield a brown oil (0.88g). This was heated at reflux in xylene (120ml) for 2h using a Dean and Stark head. The reaction mixture was evaporated to dryness under reduced pressure and purified by column chromatography (silica eluting with 5–7% methanol/chloroform, to afford the oxadiazole (E2) (0.26g, 22% from ester) which was purified as the hydrochloride salt (200mg).

$^1$H NMR (270MHz, d$_6$DMSO) δ: 1.86 (5H, bm); 2.32 (3H, s, CH3); 2.90 (1H, dd, 3-H); 3.17 (6H, m); 3.34 (1H, s); 3.43 (1H, m).

$^{13}$C NMR (67MHz, d$_6$DMSO) δ: 11.0 (CH); 18.7 (CH2); 23.4 (CH3); 23.5 (CH2); 28.5 (CH2); 30.7 (CH); 44.7 (CH2); 45:2 (CH2); 50.8 (CH2); 166.8 (quaternary C) and 177.7 (quaternary C).

MS $C_{11}H_{17}N_3O$ requires M+207.1366, M+found 207.1373.

EXAMPLE 3

(±) 3-(1,3-Oxazol-2-yl)methyl]-1-azabicyclo[2.2.2]octane oxalate salt (E3)

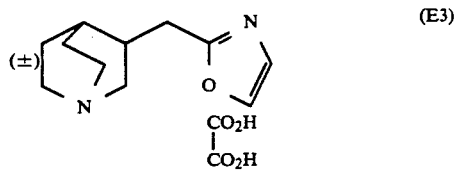

(±) 3-Aminocarbonylmethyl-1-azabicyclo[2.2.2]octane (D4, 1.6g, 0.0095mol) was mixed with vinylene carbonate (1.25g, 0.0145mol) and polyphosphoric acid (34g), and the mixture heated at 110–130° C. for 90 minutes. The solution was cooled, ice (50ml) added and the slurry stirred at room temperature for 1h. The ice-cooled reaction mixture was then basified to pH 9 with 20% aqueous NaOH solution. The ice-cooled solution was then saturated with solid potassium carbonate and extracted with diethyl ether (2×500ml). The organic extracts were dried ($Na_2SO_4$), filtered and evaporated to dryness under reduced pressure to yield a yellow oil This was purified by column chromatography (neutral alumina eluting with 1% MeOH/CHCl$_3$) to afford a clear oil (280mg, 16%) which was crystallised as the oxalate salt to afford the title compound.

$^1$H NMR (270MHz, d$_6$DMSO) δ: 1.86 (5H, bm); 2.96 (4H, m); 3.22 (4H, bm); 3.48 (1H, dt); 7.15 (1H, s, oxazole-H); 8.06 (1H, s, oxazole-H).

$^{13}$C NMR (67MHz, d$_6$DMSO) δ: 17.6, 23.4. 23.7. 30.1. 31.2, 45 0, 45.7, 51.2, 126.9 (CH-oxazole), 139.4 (CH-oxazole), 162.2 (C-oxazole), 164.0 (C oxalate).

MS $C_{11}H_{16}N_2O$ requires M+192.1262; M+found 192.1263.

EXAMPLE 4

(±)
5-[(3-Amino-1,2,4-oxadiazol-5-yl)methyl]-1-azabicyclo[3.2.1]octane (E4)

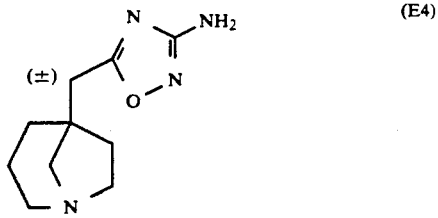

To a solution of sodium (1.0g, 0.04 mole) in ethanol (60ml) under an atmosphere of nitrogen was added crushed molecular sieve (5g) and hydroxyguanidine sulphate hemihydrate (5.75g, 0.04 mole). The resulting slurry was stirred for 15 min then (±) 5-(methoxycarbonylmethyl)-1-azabicyclo[3.2.1]octane (D11, 0.5g, 0.0027 mole) was added. The mixture was heated under reflux for 6h then left to stand overnight. The reaction was neutralized with acetic acid, filtered and concentrated in vacuo to a gum. The gum was partitioned between saturated aqueous potassium carbonate and chloroform. The organic phase was separated, dried (Na$_2$SO$_4$) and evaporated to afford a gummy solid. Recrystallised from methanol/ether to afford the title compound (E4, 0.13g, 0.006 mole, 23%).

$^1$H NMR (CDCl$_3$) δ: 1.4–1.85 (6H, m), 2.61–3.13 (6H, m), 2.92 (2H, s, 9-CH$_2$), 4.43 (broad singlet).

$^{13}$C NMR (CDCl$_3$) δ: 20 (CH$_2$), 35.3 (CH$_2$), 35.5 (CH$_2$), 36 (CH$_2$), 42.5 (tertiary C C-5), 52 (CH$_2$), 54.8 (CH$_2$), 65 (CH$_2$), 167.9, 177.5 together (oxadiazole carbons).

EXAMPLE 5

(±) endo
3-[(3-Amino-1,2,4-oxadiazol-5-yl)methyl]-1-azabicyclo[2.2.1]heptane (E5)

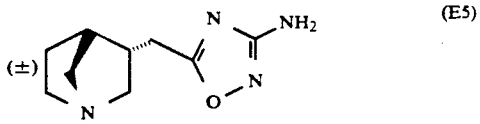

Sodium (420mg, 0.018 moles) was dissolved in ethanol (50ml) under an atmosphere of nitrogen and the resulting solution cooled to 20° C. and treated with hydroxy guanine hemihydrate (1.4g, 0.005 moles) and powdered 3A molecular sieve (5g). To this well stirred slurry was added (±) endo 3-ethoxycarbonylmethyl-1-azabicyclo[2.2.1]heptane (D6) and the reaction heated under reflux for 2h. The reaction was then neutralised by the addition of glacial acetic acid, filtered through celite and the filtrate concentrated in vacuo to a gum. This gum was partitioned between chloroform and saturated aqueous potassium carbonate solution and the organic phase separated and concentrated in vacuo to a gum. Crystallisation from acetone/methanol afforded the title compound (E5) as needles mpt 140–145° C. (185mg, 36%).

$^1$H NMR (270MHz, CD$_3$OD) 1.46–1.75 (2H, m), 2.05–2.18 (1H, m), 2.4–2.64 (5H, m), 2.75–2.85 (1H, m), 2.85 (2H, d, J=7Hz), 3.0–3.13 (1H, m), 4.9 (2H, s).

$^{13}$C NMR CD$_3$OD δ: 23.7, 28.4, 39.3, 42.0, 54.9, 60.4, 61.5, 170.5, 179.5

Analysis C$_9$H$_{14}$N$_4$O, requires C, 55.6; H, 7.3; N, 28.8%

Found C, 55.6; H, 7.3; N, 28.7%.

EXAMPLE 6

(±) endo 3-(3-Methyl-1,2.4-oxadiazol-5-yl)methyl-1-azabicyclo[2.2.1]heptane oxalate salt (E6)

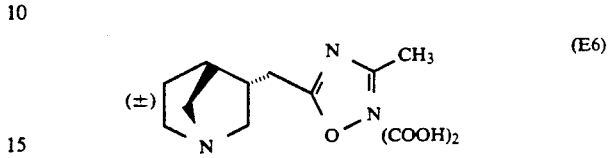

(±) endo 3-(Ethoxycarbonylmethyl)-1-azabicyclo[2.2.1]heptane (D6) (1.15g, 0.006moles) was heated under reflux in concentrated hydrochloric acid (15ml) and water (7ml) for 2h. The reaction mixture was evaporated to constant volume, dry toluene (20ml) added and the mixture re-evaporated to remove last traces of water. The dry residue was dissolved in thionyl chloride (15ml) and heated under reflux for 2 minutes. The solution was then concentrated in vacuo and azeotroped twice with dry toluene to afford the thionyl chloride free acid chloride. The acid chloride was dissolved in ethanol free chloroform (30ml) and treated with acetamide oxime (0.74g, 0.01 moles) under an atmosphere of nitrogen; the reaction mixture was heated under reflux for 2 hours and then left to stand for 48h. The reaction was basified with saturated aqueous potassium carbonate solution and the organic phase separated, dried (Na$_2$SO$_4$) and concentrated to yield a brown oil. The brown oil was heated under reflux in xylene (100ml) for 1.75h. Xylene was removed in vacuo to afford a dark brown oil. The crude oil was chromatographed on silica in a gradient of 5 to 10% methanol in chloroform to afford the title compound as a colourless oil (400mg, 33%). The oxalate salt crystallised from ether as cubes which contained 10% of the exo isomer by NMR. m.p. 104–107° C.

Oxalate salt $^1$H NMR (CD$_3$OD) δ: 2.74–3.01 (2H, m), 3.28 (3H, s, CH3), 3.47–3.51 (1H, m), 3.75–3.89 (3H, m), 3.95–4.60 (6H, m).

Oxalate salt $^{13}$C NMR (CD$_3$OD) (Major isomer), δ: 12.7, 22.7, 27.7, 36.8, 40.8, 53.4, 57.7, 60.8, 166.3 (oxalate), 168.31, 179.7.

EXAMPLE 7

(±) endo
3-(1,3-Oxazol-2-yl)methyl]-1-azabicyclo[2.2.1]heptane oxalate salt (E7)

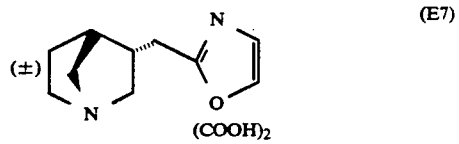

Crude (±) endo 3-ethoxycarbonylmethyl-1-azabicyclo[2.2.1]heptane (D6) (1.21g, 0.0066 mols) was dissolved in concentrated hydrochloric acid (15ml) and water (6ml) and heated under reflux for 2h. Water and excess hydrochloric acid were removed in vacuo, dry toluene (30ml) was added to the residue and the mixture re-evaporated to remove last traces of water. The dry residue was treated with thionyl chloride (11ml) and dichloromethane (30ml) and heated under reflux for 1h when a homogenous solution was attained. The reaction mixture was evaporated to afford a pale brown oil which was azeotroped three times with toluene. A solution of the dry oil in dichloromethane (30ml) was cooled to −40° C. and treated dropwise with a saturated solution of ammonia in dichloromethane (40ml) under an atmosphere of nitrogen. The reaction mixture was allowed to warm to room temperature with stirring. The mixture was basified with saturated aqueous potassium carbonate, the organic phase separated, dried (Na₂SO₄) and concentrated in vacuo to afford a gummy solid. Crystallization from acetone/ether gave the amide as a buff coloured solid (0.83g, 0.005mols) which was used without further purification in the next step. The amide (0.79g, 0.005moles) was treated with polyphosphoric acid (34g) and vinylene carbonate (0.59g, 0.005moles) and the well stirred mixture heated at 120° C. for 1h. The resulting black liquid was allowed to cool slightly and poured into saturated aqueous potassium carbonate (50ml) and ice with vigorous stirring. The black solution was extracted with ether, the organic phase was separated, dried (Na₂SO₄) and concentrated in vacuo to yield a pale yellow oil. The oxalate salt was recrystallised from methanol/ether to afford the title compound as a white solid (210mg, 12%). m.p 136–143° C., containing 10% of the exo isomer by NMR.

Oxalate salt ¹H NMR (DMSO) δ: 1.64–2.13 (2H, m), 2.74–3.7 (10H, m), 7.2 (1H, s, 4'-CH), 8.12 (1H, s, 5'-CH).

Oxalate salt ¹³C (DMSO) (major isomer) δ: 21, 27.5, 36, 52, 56.6, 59, 127, 139.5, 163, 165 (oxalate), plus one carbon under DMSO signal.

EXAMPLE 8

(±) endo 3-(1,3-Oxazol-5-yl)methyl -1-azabicyclo[2.2.1]heptane hydrochloride salt (E8)

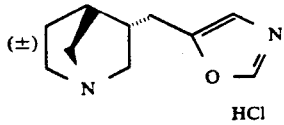

A solution of (±) endo 3-N-methyl-N-methoxy aminocarboxymethyl-1-azabicyclo[2.2.1]heptane (D7) (1.36g, 0.007 moles) in THF (40ml) was cooled to −70° C. under an atmosphere of nitrogen and DIBAL (5.1ml of a 1.5M solution in toluene, 0.008 moles) added slowly. The solution was stirred at −70° C. for 45 mins and then at room temperature for a further 2½h. The reaction mixture was re-cooled to −70° C. and then poured into a vigorously stirred mixture of 5N hydrochloride acid (7ml) and ice. The reaction mixture was evaporated in vacuo to afford an oil which was basified with saturated aqueous potassium carbonate and partitioned with chloroform. The organic phase was separated, dried (Na₂SO₄) and concentrated to give a pale brown oil. The crude oil was distilled on a Kugelröhr to yield the aldehyde as a colourless oil (0.81g, 0.06 moles) b.p. 115° C. at 0.5mmHg. Without further purification the aldehyde (0.81g, 0.006 moles) in methanol (20ml) was treated with para toluenesulphonylmethylisocyanide (TOSMIC) (1.2g, 1.1eq) and solid potassium carbonate (0.93g, 1.1eq) under nitrogen. The solution was heated under reflux for 1.5h, then concentrated in vacuo and the residual oil partitioned between saturated aqueous potassium carbonate and chloroform. The organic phase was separated, dried (Na₂SO₄) and evaporated to yield a pale brown oil. The crude oil was dissolved in ether which was added to polyphosphoric acid (18g) and the ether was evaporated in vacuo. The reaction mixture was then heated at 170° C. for 10 mins with vigorous stirring. The resulting hot, brown liquid was immediately poured into a vigorously stirred mixture of chloroform (50ml) and saturated aqueous potassium carbonate (50ml). The organic phase was separated, dried (Na₂SO₄) and evaporated to yield a crude brown oil which was distilled on a Kugelrohr to give the title compound (E11) as yellow oil (260mg, 20%) b.p. 200 at 0.5mmHg. The oil was crystallised as the hydrochloride salt—a low melting, colourless solid (300mg, 20%) containing 10% of the exo isomer by NMR.

Hydrochloride ¹H NMR (DMSO) δ: 1.85–2.10 (2H, m), 2.66–3.62 (10H, m), 7.03 (1H, s, oxazole CH), 8.36 (1H, s, oxazole CH)

Hydrochloride ¹³C NMR (DMSO) major isomer, δ: 21, 25, 36.5, 52, 56, 59, 122.5, 150.5, 151.5 plus one carbon under DMSO signal.

EXAMPLE 9

(±) endo 3-[(3-Amino-1,2,4-oxadiazol-5-yl)methyl]-1-azabicyclo[3.2.1]octane (E9)

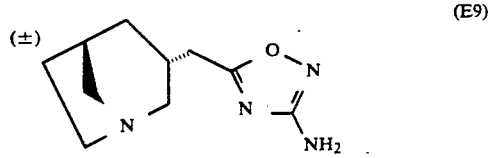

(±) E/Z 3-Ethoxycarbonylmethylene-1-azabicyclo[3.2.1]-octane (D15) (1.05g, 0.0054 moles) was dissolved in ethanol (50ml) and treated with 10% palladium on charcoal (120mg) with stirring under an atmosphere of hydrogen for 6h. The reaction was then filtered through celite and concentrated in vacuo to a gum. Kugelröhr distillation afforded the saturated ester (0.73g, 0.0038 moles) as a 10:1 mixture of endo:exo isomers which was used directly in the next step. Sodium metal (0.37g, 0.016 moles) was dissolved in dry ethanol (30ml) under nitrogen and crushed 3A molecular sieve (3g) added. Hydroxyguanidine sulphate hemihydrate (2.13g, 0.008 moles) and the saturated ester (0.4g, 0.002 moles) were added, the reaction mixture stirred at 25° C. for 15 mins and then heated under reflux for 3h. The reaction was then cooled, quenched by the addition of acetic acid and concentrated in vacuo to a gum which was partitioned between saturated aqueous potassium carbonate and chloroform. The organic phase was separated, dried (Na₂SO₄) and concentrated in vacuo to a gum. Crystallisation from ether afforded the title compound (E9) (0.081g, 0.00039 mole, 19%) as needles. M.pt. 151–153° C.

¹H NMR (CDCl₃) δ: 1.4–1.54 (1H), 1.78–1.90 (2H), 2.03–2.32 (3H), 45–2.6 (1H), 2.72–3.1 (6H), 3.24–3.38 (1H), 4.37–4.7 (2H).

¹³CC NMR CDCl₃ δ: 27.7, 31.3, 33.0, 34.3, 34.9, 52.3, 58.3, 58.8, 167.8, 178.4

EXAMPLE 10

(±) exo 3-(1,3-Oxazol-2-yl)methyl-1-azabicyclo[2.2.1]heptane oxalate salt (E10)

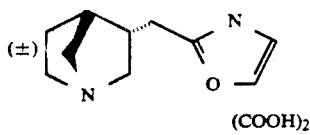

(±) exo 3-Methoxycarbonylmethyl-1-azabicyclo[2.2.1]heptane (D2) (0.250g, 0.0015 mole) was dissolved in concentrated hydrochloric acid (7ml) and water (3ml) and heated under reflux for 2h. The reaction was evaporated to dryness and azeotroped with dry toluene. The dry residue was treated with thionyl chloride (6ml) and dichloromethane (14ml) and heated under reflux for 1h. The reaction was concentrated in vacuo and azeotroped three times with dry toluene to remove last traces of thionyl chloride and afford a pale brown oil. A solution of the oil in dichloromethane (20ml) under an atmosphere of nitrogen was cooled to −40° C. The cold solution was treated, dropwise, with a saturated solution of ammonia in dichloromethane (10ml). The reaction was allowed to warm to room temperature and stir for 1h. The reaction mixture was partitioned with saturated aqueous potassium carbonate, the organic phase was separated, dried ($Na_2SO_4$) and concentrated in vacuo to afford a viscous oil. The oil was worked with ether to give the crude amide as a gummy buff-coloured solid.

The crude amide was treated with polyphosphoric acid (20g) and vinylene carbonate (0.15g, 1eq) and heated at 120° C. for 1h. The black liquid was allowed to cool slightly and was then cautiously poured into a vigorously stirred mixture of saturated aqueous potassium carbonate and ice. Solid potassium carbonate was added until all of the gummy material had dissolved. The mixture was partitioned with ether, the organic phase was separated, dried ($Na_2SO_4$) and concentrated in vacuo to afford an oil. The oil was chromatographed on silica in a gradient of 10% to 40% methanol in chloroform. Elution with 30% methanol in chloroform gave the title compound (E10) (15mg, 6%) which crystallised as the oxalate salt.

m.p. 109° C.

Oxalate $^1$H NMR (CD$_3$OD) δ: 1.9–2.03 (1H, m), 2.22–2.37 (1H, m), 2.62–2.78 (1H, m), 2.94–3.74 (9H, m), 7.26 (1H, s) and 8.3 (1H, s) together oxazole protons.

EXAMPLE 11

(±) endo 3-[(2-Methyltetrazol-5-yl)methyl]-1-azabicyclo[2.2.1]heptane oxalate salt (E11)

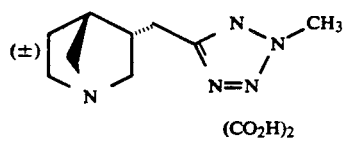

(±) endo 3-(Cyanomethyl)-1-azabicyclo[2.2.1]heptane endo:exo 10:1 (D13) (0.74g, 0.005 moles) in tetrahydrofuran (2ml, 0.0015 mole) was heated with azidotrimethylsilane in an autoclave at 110° C. for 24h. The reaction mixture was dissolved in methanol and then concentrated to remove any unreacted hydrazoic acid. The residue was then taken up in methanol and treated with an excess of diazomethane in ether at 10° C. for 1h when the yellow colour persisted. The reaction was then concentrated in vacuo to a gum. The gum was extracted with ethyl acetate and the extract columned on neutral alumina in a gradient of 0–20% methanol in ethyl acetate. Elution with ethyl acetate afforded a mixture of unreacted endo and exo starting materials D13 (40mg). Elution with 2% methanol in ethyl acetate afforded the 2 methyl isomer (163mg) 10:1 mixture of endo:exo isomers as a colourless oil. The oxalate salt crystallized from acetone/ether to afford the title compound (E11) (138mg, 0.00049 mole, 10%) as needles M.pt 121–124° C. Elution with 10% methanol in ethyl acetate afforded a 10:1 mixture of endo and exo [(1-methyltetrazol-5-yl)methyl-1-azabicyclo[2.2.1]-heptane (60mg).

$^1$H NMR (CD$_3$OD) (exo isomer) δ: 2.15–2.30 and 2.30–2.45 each (1H, m, 5-H), 3.03–3.72 (9H, m), 3.8–3.95 (1H, m), 4.5 (3H, s, CH$_3$).

$^{13}$C NMR CD$_3$OD (exo isomer) δ: 22.2 and 26.5 (C-5 and C-8), 38.4, 39.77 and 40.73 (C-3, C-4, CH3), 53.9, 58.6, 61.0 (C-2, C-6, C-7), 166, oxalate (C-5).

Analysis % Found: C, 46.5; H, 6.0; N, 24.6
$C_{11}H_{17}N_5O_4$ requires: C, 46.6; H, 6.1; N, 24.7%

EXAMPLE 12

(±) 5-[(Fur-2-yl)methyl-1-azabicyclo[3.2.1]octane oxalate salt (E12)

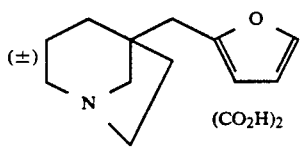

A stirred solution of 5-[(fur-2-yl)hydroxymethyl]-1-azabicyclo[3.2.1]octane (D14, 600mg, 0.0029 mole) and triethylsilane (1.85ml, 0.012 mole) in dry acetonitrile (60ml) at 0° C. under nitrogen was treated with tin (IV) chloride (0.75ml, 0.0064 mole). The resulting brown solution was allowed to warm to room temperature over 20 minutes, then heated at 40° C. for 30 minutes. The solution became almost colourless. The solution was cooled in an ice bath and treated with excess concentrated potassium carbonate solution, then extracted with ethyl acetate. The extract was concentrated in vacuo and the residue partitioned between ethyl acetate and dilute hydrochloric acid. The acid layer was separated, basified with potassium carbonate solution and extracted with ethyl acetate. The extract was dried ($Na_2SO_4$) and concentrated in vacuo to leave a yellow oil, which was distilled in a Kugelröhr apparatus (bp 170° C. at 0.2mmHg) to give a colourless oil. This was converted into its oxalate salt, which was recrystallised from acetone/ether to give the title compound (E12) as a white solid (50mg, 6%) m.pt. 129–133° C.

Oxalate salt: $^1$H NMR (d$_6$ DMSO) δ: 1.45–1.55 (2H, m), 1.65–2.05 (4H, m), 2.80 (2H, s), 3.00–3.25 (4H, m), 3.25–3.50 (2H, m), 6.18–6.22 (1H, m), 6.38–6.42 (1H, m), 7.57–7.60 (1H, m).

EXAMPLE 13

4-[(3-Amino-1,2,4-oxadiazol-5-yl)methyl]-1-azabicyclo[2.2.1]heptane (E13)

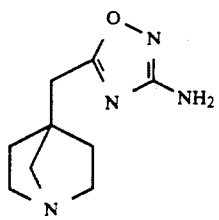
(E13)

Sodium (850mg, 37mM) was dissolved in ethanol (50ml) under an atmosphere of nitrogen. The solution was then treated with hydroxyguanine sulphate hemihydrate (2.55g, 0.0192 mole), powdered 3A molecular size (10g) and 4-(ethoxycarbonylmethyl)-1-azabicyclo[2.2.1]heptane (D26) (0.85g, 0.0046 mole) and heated under reflux for 1.5h. Acetic acid (3ml) was added, the solution filtered through celite and the filtrate concentrated in vacuo to a gum. The gum was then partitioned between chloroform and saturated aqueous potassium carbonate solution. The organic phase was separated, dried over sodium sulphate and concentrated in vacuo to a gum. The gum was crystallised from ether to afford the title compound (E13) (310mg, 0.0016 mole, 34%) as needles. M.pt 144–145° C.

$^1$H NMR (CDCl$_3$) δ: 1.28–1.43 (2H, m, 3H, 5H), 1.53–1.67 (2H, m, 3H, 5H), 2.4 (2H, s, 7-CH$_2$), 2.55–2.7 (2H, m, 2H, 6H), 2.9–3.05 (2H, m, 2H, 6H), 3.15 (2H, s, 8-CH$_2$).

$^{13}$C NMR (CDCl$_3$) δ: 29.6 (C-8), 35.5 (C-3, C-5), 47.7 (C-6), 55.4 (C-2, C-2), 63.9 (C-7), 167.9 and 177.7 (C-3', C-5').

EXAMPLE 14

4-[(1,3-Oxazol-2-yl)methyl]-1-azabicyclo[2.2.1]heptane oxalate salt (E14)

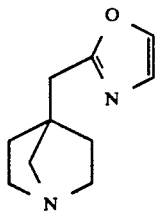
(E14)

4(Aminocarbonylmethyl)-1-azabicyclo[2.2.1]heptane (D27) (350mg, 0.00227 mole) in polyphosphoric acid (15g) was treated with vinylene carbonate (292mg, 0.0034 mole) with continuous stirring and the solution heated on an oil bath at 120° C. for 1.5h. The reaction was then allowed to cool and poured into aqueous saturated potassium carbonate solution. The product was recovered by extraction into chloroform. The organic phase was separated, dried over sodium sulphate and concentrated in vacuo to a gum (48mg). The gum was dissolved in ether, filtered through a short column of decolourising charcoal and treated with oxalic acid (25mg) in methanol. The solution was allowed to crystallise to afford the title compound (E14) (45mg, 0.00017 moles, 7%) as needles. M.pt. 140–143° C.

$^1$H NMR (CD$_3$OD) δ: 1.82–1.95 (2H, m, 3H, 5H), 2.0–2.15 (2H, m, 3H, 5H), 3.28 (2H, s, 7-CH$_2$), 3.32 (2H, s, 8-CH$_2$), 3.35 (2H, m, 2H, 6H), 3.5–3.65 (2H, m, 2H, 6H), 7.18 (1H, s, 4'H), 7.92 (1H, s, 5'H).

$^{13}$C NMR (CD$_3$OD) δ: 30.2 (C-8), 32.8 (C3, C5), 48.2 (C-4), 54.5 (C2, C6), 62.5 (C-7), 127.8 (C-4'), 141.1 (C-5'), 163.3 (oxalate), 166.5 (C-2').

EXAMPLES 15 and 16

(±) endo 3-[(5-Methyl-1,2,4-oxadiazol-3-yl)methyl-1-azabicyclo[2.2.11]heptane hydrochloride salt (E15)

(±) exo 3-[(5-Methyl-1,2,4-oxadiazol-3-yl)methyl)-1-azabicyclo[2.2.1]heptane hydrochloride salt (E16)

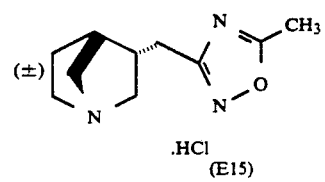
.HCl
(E15)

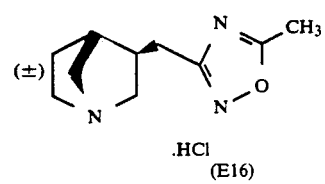
.HCl
(E16)

(±) 3-[(N-Acetoxy)-carboximidamide methyl]-1-azabicyclo[2.2.1]heptane (D29) (0.42g, 0.002 mole in toluene, 50ml) was heated under relux using a Dean and Stark apparatus for 12h. The solution was then concentrated in vacuo to a gum and the residue columned on silica in a gradient of 5–8% methanol in chloroform. Elution with 5% methanol in chloroform afforded a colourless oil which was dissolved in ether and treated with hydrogen chloride in ether. The resulting solid was recrystallised from methanol/ether to afford the title compound (E16) (42mg, 0.00018 mole) as needles. M.p. 165–167° C.

$^1$H NMR ((CD$_3$)$_2$SO) δ: 1.70–1.82 (1H, m), 2.03–2.2 (1H, m), 2.42–2.55 (1H, m), 2.75 (3H, s), 2.8–3.6 (9H, m).

$^{13}$C NMR ((CD$_3$)$_2$SO) δ: 11.9 (CH$_3$), 27.3, 28.8 (C-5 and C-8), 37.7, 39.2 (C-3 and C-4), 50.8, 55.7, 57.4 (C-2, C-6, C-7), 168.5, 176.9 (C-3' and C-5').

Elution with 8% methanol in chloroform afforded a colourless oil which was dissolved in ether and treated with hydrogen chloride in ether to afford a gummy solid. Recrystallisation from methanol/ether afforded the title compound (E15) (0.151g, 0.00066 mole) as needles. M.p. 193–195° C.

$^1$H NMR ((CD$_3$)$_2$SO) δ: 1.79–1.99 (2H, m), 2.55 (3H, s, CH$_3$), 2.68–3.55 (10H, m).

$^{13}$C NMR ((CD$_3$)$_2$SO) δ: 11.8 (CH$_3$), 20.9 and 25.6 (C-5, C-8), 35 5 and 39.2 (C-3, C-4), 51.7, 56.2 and 59.0 (C-2, C-6, C-7), 168.8 and 176.9 (C-3', C-5').

EXAMPLE 17

(±) 3-((1,3-Thiazol-2-yl)methyl)-1-azabicyclo[2.2.2]octane oxalate salt (E17)

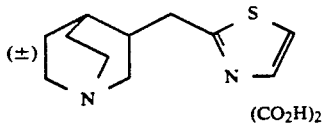

(±) Z 3((1,3-Thiazol-2-yl)methylene)-1-azabicyclo[2.2.2]octane (D34) (0.15g, 0.00073 moles) was hydrogenated in methanol (20ml) over a 5% platinum on sulphided carbon catalyst (0.6g) at 200 psi and 100° C. for 48h. The mixture was filtered through Kieselguhr and the filter pad washed with methanol (2×50ml). The combined filtrates were concentrated in vacuo and the residue subjected to column chromatography on TLC alumina eluting with 0.5% methanol/chloroform. This gave a white solid which was treated with anhydrous oxalic acid in ethanol/diethylether to give the title compound (E17) (0.03g, 14%) m.p. 126–130° C.

Free base $^1$H NMR (CDCl$_3$) δ: 1.40–1.87 (5H, m), 2.12–2.25 (1H, m), 2.44–2.53 (1H, m), 2.71–2.93 (5H, m), 3.10 (2H, d), 7.19 (1H, d), 7.69 (1H, d).

BIOLOGICAL ACTIVITY

Radio ligand Binding

Cerebral cortex from Hooded Lister rats (Olac, UK) is homogenised in 2.5 vols ice-cold 50mM tris buffer pH 7.7 (at 25° C.). After centrifugation at 25,000 × g at 4° C. for 15 min the pellet is resuspended in 2.5 vols buffer and the wash repeated 3 times more. The final resuspension is in 2.5 volumes and the homogenates are stored in 1ml aliquots at −20° C.

Incubations (total volume 2ml) are prepared using the above buffer with the addition of 2mM magnesium chloride in the 3H-Oxotremorine-M (3H-OXO-M) experiments. For 3H-Quinuclidinyl Benzilate (3H-QNB), 1ml of stored membranes is diluted to 30ml and 0.1ml mixed with test compound and 0.27nM (c. 25,000 cpm) 3H-QNB (Amersham International). For 3H-OXO-M, 1ml of membranes is diluted to 6ml and 0.1ml mixed with test compound and 2nM (c. 250,000 cpm) 3H-OXO-M (New England Nuclear).

Non-specific binding of 3H-QNB is defined using 1μM Atropine sulphate (2μM Atropine) and of 3H-OXO-M using 10μM Oxotremorine. Non-specific binding values typically are 5% and 25% of total binding, respectively. Incubations are carried out at 37° C. for 30 min and the samples filtered using Whatman GF/B filters. (In the 3H-OXO-M experiments the filters are presoaked for 30 min in 0.05% polyethylenimine in water). Filters are washed with 3×4ml ice-cold buffer. Radioactivity is assessed using a Packard BPLD scintillation counter, 3ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H-OXO-M and the muscarinic antagonist 3H-QNB. The ratio IC$_{50}$(3H-QNB)/IC$_{50}$(3H-OXO-M) gives an indication of the agonist character of the compound. Agonists typically exhibit a large ratio; antagonists typically exhibit a ratio near to unity.

The results are shown in Table 1.

TABLE 1

| Example | [$^3$H-OXO-M IC$_{50}$ (nM) | $^3$H-QNB IC$_{50}$ (nM) |
|---|---|---|
| E1 | 36.5 | 7,500 |
| E2 | 1,050 | 13,000 |
| E3 | 755 | 7,000 |
| E4 | 580 | 6,700 |
| E5 | 32 | 21,000 |
| E6 | 150 | 10,200 |
| E7 | 42 | 8,000 |
| E8 | 625 | 38,000 |
| E9 | 925 | 4,600 |
| E10 | 38 | 5,600 |
| E11 | 340 | 8,000 |
| E12 | 660 | 4,000 |
| E13 | 118 | 85,000 |
| E14 | 410 | 74,000 |
| E15 | 950 | 30,500 |
| E16 | 1000 | — |
| E17 | 875 | — |

We claim:

1. A compound of formula (I) or a pharmaceutically acceptable salt thereof:

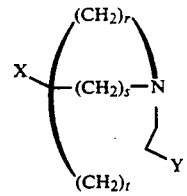

in which one of X and Y represents hydrogen and the other represents —CH$_2$—Z where Z is a group

in which Q represents a 3-membered divalent residue completing a 5-membered aromatic ring and comprises one or two heteroatoms selected from oxygen, nitrogen and sulphur, or three nitrogen atoms, any amino nitrogen being optionally substituted by a C$_{1-2}$ alkyl, cyclopropyl or propargyl group, and any ring carbon atom being optionally substituted by a group R$_1$; or a group

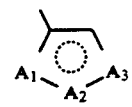

in which A$_1$, A$_2$ and A$_3$ complete a 5-membered aromatic ring and A$_1$is oxygen or sulphur, one of A$_2$ and A$_3$ is CR$_2$ and the other is nitrogen or CR$_3$, or A$_2$ is oxygen or sulphur, one of A$_1$and A$_3$ is CR$_2$ and the other is CR$_3$; and R$_1$, R$_2$ and R$_3$ are independently selected from hydrogen, halogen, CN, OR$_4$, SR$_4$, N(R$_4$)$_2$, NHCOR$_4$, NHCOOCH$_3$, NHCOOC$_2$H$_5$, NHOR$_4$, NHNH$_2$, NO$_2$, COR$_4$, COR$_5$, C$_{2-4}$ alkenyl, C$_{2-4}$ alkynyl, cyclopropyl or C$_{1-2}$ alkyl optionally substituted with OR$_4$, N(R$_4$)$_2$, SR$_4$, CO$_2$R$_4$, CON(R$_4$)$_2$ or one, two or three halogen atoms, in which each R$_4$ is independently hydrogen or C$_{1-2}$ alkyl and R$_5$ is OR$_4$, NH$_2$ or NHR$_4$; r represents, an integer of 2 s represents an integer of 1 and t represents 0.

2. A compound according to claim 1 wherein the 5-membered aromatic ring is selected from 1,2,4-oxadiazol-5-yl, 1,2,4-oxadiazol-3-yl, 1,3,4-oxadiazol-2-yl, 1,3-oxazol-2-yl, 1,3-oxazol-4-yl 1,3-oxazol-5-yl, 1,2-oxazol-3-yl, 1,2-oxazol-5-yl, 1,2,4-thiadiazol-5-yl, 1,3,4-thiadiazol-2-yl, 1,3-thiazol-2-yl, 1,3-thiazol-5-yl, 1,2-thiazol-5-yl, furan-2-yl, furan-3-yl, 1,2,3-triazol-4-yl and 2H-tetrazol-5-yl.

3. A compound according to claim 1, wherein $R_1$, $R_2$ and $R_3$ are independently selected from hydrogen, halogen, $N(R_4^1)_2$, $C_{2-3}$ alkenyl, $C_{2-3}$ alkynyl, cyclopropyl or $C_{1-2}$ alkyl optionally substituted with one, two or three fluorine atoms, in which $R_4^1$ is hydrogen or methyl.

4. A compound according to claim 3 wherein $R_1$, $R_2$ and $R_3$ are selected from hydrogen and methyl.

5. A compound according to claim 1, where Z is selected from 3-amino-1,2,4-oxadiazol-5-yl, 3-methyl-1,2,4-oxadiazol-5-yl, 1,3-oxazol-2-yl, 1,3-oxazol-5-yl, 2-methyl-2H-tetrazol-5-yl, 2-furyl, 5-methyl-1,2,4-oxadiazol-3-yl and 1,3-thiazol-2-yl.

6. A compound according to claim 1, wherein X is hydrogen.

7. (±) exo 3-[(3Amino-1,2,4-oxadiazol-5-yl) methyl]-1-azabicyclo[2.2.1]heptane, [(±)3-[(3-methyl-1,2,4-oxadiazol-5-yl)methyl]-1-azabicyclo[2.2.2]octane];
[(±)-[(1,3-oxazol-2-yl)methyl]-1-azabicyclo [2.2.2]octane];
[(±) 5-[(3-amino-1,2,4-oxadiazol-5-yl)methyl]-1-azabicyclo[3.2.1]octane];
(±) endo 3-[(3-amino-1,2,4-oxadiazol-5-yl)methyl]-1-azabicyclo[2.2.1]heptane,
(±) endo 3-[(3-methyl-1,2,4-oxadiazol-5-yl)methyl]-1-azabicyclo[2.2.1]heptane,
(±) endo 3-[(1,3-oxazol-2-yl)methyl]-1-azabicyclo[2.2.1]heptane,
(±) endo 3-[(1,3-oxazol-5-yl)methyl]-1-azabicyclo[2.2.1]heptane,
(±) exo 3-[(1,3-oxazol-2-yl)methyl]-1-azabicyclo[2.2.1]heptane,
(±) endo 3-[(2-methyltetrazol-5-yl)methyl]-1-azabicyclo[2.2.1]heptane,
4-[(3-amino-1,2,4-oxadiazol-5-yl)methyl]-1-azabicyclo[2.2.1]heptane,
4-[(1,3-oxazol-2-yl)methyl]-1-azabicyclo[2.2.1]heptane,
(±) endo 3-[(5-methyl-1,2,3-oxadiazol-3-yl)methyl]-1-azabicyclo[2.2.1]heptane,
(±) exo 3-[(5-Methyl-1,2,3-oxadiazol-3-yl)methyl]-1-azabicyclo[2.2.1]heptane,
or a pharmaceutically acceptable salt of any of the foregoing compounds.

8. A pharmaceutical composition for the treatment and/or prophylaxis of dementia in mammals, which comprises an effective amount of a compound of formula (I) as defined in claim 1 or a pharmaceutically acceptable salt thereof, and a pharmaceutically acceptable carrier.

9. A method of treatment and/or prophylaxis of dementia in mammals including humans, which comprises administering to the sufferer an effective amount of a compound of formula (I) as defined in claim 1 or a pharmaceutically acceptable salt thereof.

* * * * *

UNITED STATES PATENT AND TRADEMARK OFFICE
CERTIFICATE OF CORRECTION

PATENT NO. : 5,091,397

DATED : February 25, 1992

INVENTOR(S) : Harry J. Wadsworth, Michael S. Hadley, Paul A. Wyman and Sarah M. Jenkins It is certified that error appears in the above-identified patent and that said Letters Patent is hereby corrected as shown below:

In Claim 7, in column 45, from line 26 to line 31, delete:

[(±)3-[(3-methyl-1,2,4-oxadiazol-5-yl)methyl]-1-azabicyclo[2.2.2]octane];
[(±)-[1,3-oxazol-2-yl)methyl]-1-azabicyclo [2.2.2]octane];
[(±) 5-[(3-amino-1,2,4-oxadiazol-5-yl)methyl]-1-azabicyclo[3.2.1.]octane];

UNITED STATES PATENT AND TRADEMARK OFFICE
CERTIFICATE OF CORRECTION

PATENT NO. : 5,091,397

DATED : February 25, 1992

INVENTOR(S) : Harry J. Wadsworth, Michael S. Hadley, Paul A. Wyman and Sarah M. Jenkins It is certified that error appears in the above-indentified patent and that said Letters Patent is hereby corrected as shown below:

In Claim 1, the formula at line 30 in column 44 should appear as:

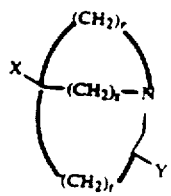

Signed and Sealed this

Second Day of November, 1993

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,091,397

DATED : February 25, 1992

INVENTOR(S) : Harry J. Wadsworth, et al.

It is certified that error appears in the above-identified patent and that said Letters Patent is hereby corrected as shown below:

Column 44:

In Claim 1, the formula at line 40 in column 44 should appear as:

and at line 1 in column 45, after "an integer of 2" add a comma.

Column 45:

In Claim 7, at line 26 in column 45, the line should read:

UNITED STATES PATENT AND TRADEMARK OFFICE
CERTIFICATE OF CORRECTION

PATENT NO. : 5,091,397
DATED : February 25, 1992
INVENTOR(S) : Harry J. Wadsworth, et al.

It is certified that error appears in the above-indentified patent and that said Letters Patent is hereby corrected as shown below:

(±) exo 3-[(3-Amino-1,2,4-oxadiazol-5-yl)methyl]-

Signed and Sealed this

Twenty-first Day of December, 1993

Attest:

BRUCE LEHMAN

Attesting Officer      Commissioner of Patents and Trademarks